United States Patent
McCrae et al.

(10) Patent No.: US 11,661,447 B2
(45) Date of Patent: May 30, 2023

(54) HUMAN β2-GLYCOPROTEIN I EXPRESSION

(71) Applicant: The Cleveland Clinic Foundation, Cleveland, OH (US)

(72) Inventors: Keith McCrae, Cleveland, OH (US); Sergei Merkulov, Cleveland, OH (US); Ravi K. Alluri, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 439 days.

(21) Appl. No.: 16/635,796

(22) PCT Filed: Aug. 3, 2018

(86) PCT No.: PCT/US2018/045145
§ 371 (c)(1),
(2) Date: Jan. 31, 2020

(87) PCT Pub. No.: WO2019/028336
PCT Pub. Date: Feb. 7, 2019

(65) Prior Publication Data
US 2020/0291093 A1    Sep. 17, 2020

Related U.S. Application Data

(60) Provisional application No. 62/540,663, filed on Aug. 3, 2017.

(51) Int. Cl.
C07K 14/775     (2006.01)
C07K 16/18      (2006.01)
C12N 15/64      (2006.01)
G01N 33/543     (2006.01)
G01N 33/68      (2006.01)

(52) U.S. Cl.
CPC ............ *C07K 14/775* (2013.01); *C07K 16/18* (2013.01); *C12N 15/64* (2013.01); *G01N 33/54306* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 5,352,803 A | 10/1994 | Mattingly | |
| 5,359,093 A | 10/1994 | Adamczyk et al. | |
| 5,496,925 A | 3/1996 | Mattingly | |
| 5,573,904 A | 11/1996 | Mattingly | |
| 5,593,896 A | 1/1997 | Adamczyk et al. | |
| 6,858,210 B1* | 2/2005 | Marquis | C07K 14/775 424/193.1 |
| 7,186,815 B2 | 3/2007 | Ravn et al. | |
| 2005/0004351 A1 | 1/2005 | Marquis et al. | |
| 2005/0282181 A1 | 12/2005 | Yan et al. | |
| 2009/0068207 A1 | 3/2009 | Breitbart et al. | |
| 2009/0161828 A1 | 6/2009 | Katzen et al. | |
| 2009/0274699 A1 | 11/2009 | Cosman | |
| 2012/0258097 A1 | 10/2012 | Baum et al. | |
| 2014/0004127 A1* | 1/2014 | Welcher | A61P 13/00 530/389.2 |
| 2016/0145303 A1 | 5/2016 | He et al. | |
| 2016/0311886 A1 | 10/2016 | Thorpe et al. | |

FOREIGN PATENT DOCUMENTS

WO    WO 2009/000538    12/2008

OTHER PUBLICATIONS

International Search Report and Written Opinion for PCT/US2018/045145, dated Oct. 22, 2018. 22 pages.
Extended European Search Report for PCT/U.S. Pat. No. 2018045145, dated Oct. 5, 2021. 8 pages.
Adamczyk et al., Chemiluminescence quenching of pteroic acid-N-sulfonyl-acridinium-9-carboxamide conjugates by folate binding protein. Bioorg Med Chem Lett. May 3, 2004;14(9):2313-7.
Adamczyk et al., Chemiluminescent acridinium-9-carboxamide boronic acid probes: application to a homogeneous glycated hemoglobin assay. Bioorg Med Chem Lett. Mar. 1, 2006;16(5):1324-8.
Adamczyk et al., Intrinsic factor-mediated modulation of cyanocobalamin-N-sulfonyl-acridinium-9-carboxamide chemiluminescence. Bioorg Med Chem Lett. Aug. 2, 2004;14(15):3917-21.
Adamczyk et al., Regiodependent luminescence quenching of biotinylated N-sulfonyl-acridinium-9-carboxamides by avidin. Org Lett. Oct. 16, 2003;5(21):3779-82.
Dalton et al., Over-expression of secreted proteins from mammalian cell lines. Protein Sci. May 2014;23(5):517-25.
Database Geneseq. Fusion protein related N-terminal signal peptide, seq ID 11. Retrieved from EBI accession No. GSP:AUM16428. 2009. 1 page.
Guler-Gane et al., Overcoming the Refractory Expression of Secreted Recombinant Proteins in Mammalian Cells through Modification of the Signal Peptide and Adjacent Amino Acids. PLoS One. May 19, 2016;11 (5):e0155340. 15 pages.
Igarashi et al., Human beta2-glycoprotein I as an anticardiolipin cofactor determined using mutants expressed by a baculovirus system. Blood. Apr. 15, 1996;87(8):3262-70.
Liu et al., Enhanced production of secretory glycoprotein VSTM1-v2 with mouse IgGK signal peptide in optimized HEK293F transient transfection. J Biosci Bioeng. Feb. 2016;121(2):133-9.
Mascarenhas et al., Signal Peptide Optimization: Effect on Recombinant Monoclonal IgG Productivity, Product Quality and Antigen-Binding Affinity. SAFC/Sigma Aldrich. 2009. 1 page.

(Continued)

*Primary Examiner* — Adam Weidner
(74) *Attorney, Agent, or Firm* — Casimir Jones, S.C.; Jason R. Bond

(57) ABSTRACT

Provided herein are compositions, systems, kits, and methods for expressing a peptide of interest, such as Apolipoprotein H (ApoH), also known as β2-glycoprotein I (β2GPI), at increased levels using a non-ApoH signal peptide (e.g., a signal peptide that permits increased protein export from cells). Also provided herein are compositions, systems, kits, and methods for employing such recombinant ApoH with a non-ApoH signal peptide to detect subject Apolipoprotein H antibodies in a sample from a subject (e.g., to diagnose antiphospholipid syndrome in a subject).

8 Claims, 23 Drawing Sheets
Specification includes a Sequence Listing.

(56) References Cited

OTHER PUBLICATIONS

Samour et al., Recombinant beta 2-Glycoprotein I (beta 2GPI) produced using a novel lentiviral approach functions at least as well as plasma-derived beta 2GPI in detection of anti-beta 2GPI antibodies. Blood. 2016: 128(22): 2596. 3 pages.

Wang et al., Efficient production of CYTL1 protein using mouse IgGK signal peptide in the CHO cell expression system. Acta Biochim Biophys Sin (Shanghai). Apr. 2016;48(4):391-4.

* cited by examiner

FIG. 1

A.      Human Apolipoprotein H Amino Acid Sequence with Signal Peptide (SEQ ID NO:1)

```
  1 mispvlilfs sflchvaiag rtcpkpddlp fstvvplktf yepgeeitys ckpgyvsrgg
 61 mrkficpltg lwpintlkct prvcpfagil engavryttf eypntisfsc ntgfylngad
121 sakcteegkw spelpvcapi icpppsiptf atlrvykpsa gnnslyrdta vfeclpqham
181 fgndtitctt hgnwtklpec revkcpfpsr pdngfvnypa kptlyykdka tfgchdgysl
241 dgpeeiectk lgnwsampsc kasckvpvkk atvvyqgerv kiqekfkngm lhgdkvsffc
301 knkekkcsyt edaqcidgti evpkcfkehs slafwktdas dvkpc
```

B.      Human Apolipoprotein H Amino Acid Sequence (SEQ ID NO:2)

```
  1 grtcpkpddl pfstvvplkt fyepgeeity sckpgyvsrg gmrkficplt glwpintlkc
 61 tprvcpfagi lengavrytt feypntisfs cntgfylnga dsakcteegk wspelpvcap
121 iicpppsipt fatlrvykps agnnslyrdt avfeclpqha mfgndtitct thgnwtklpe
181 crevkcpfps rpdngfvnyp akptlyykdk atfgchdgys ldgpeeiect klgnwsamps
241 ckasccklpvk katvvyqger vkiqekfkng mlhgdkvsff cknkekkcsy tedaqcidgt
301 ievpkcfkeh sslafwktda sdvkpc
```

FIG. 2

A.  Native Human Domain-1 of ApoH: (SEQ ID NO:3)

RTCPKDDLPFSTVVPLKTFYEPGEEITYSCKPGYVS<u>RGGMR</u>KFICPLTGLWPINTLKCTP

B.  Deletion Mutant of Human Domain-1 of ApoH: (SEQ ID NO:4)

GYVS<u>RGGMR</u>KFIC

C.  Deletion Mutant of Human Domain-1 of ApoH: (SEQ ID NO:5)

PGYVS<u>RGGMR</u>KFICP

D.  Deletion Mutant of Human Domain-1 of ApoH: (SEQ ID NO:22)

TYSCKPGYVS<u>RGGMR</u>KFICPLTGLW

E.  Deletion Mutant of Human Domain-5 of ApoH: (SEQ ID NO:23)

VSFFC<u>KNKEKKCSY</u>TEDAQC

F.  Deletion Mutant of Human Domain-5 of ApoH: (SEQ ID NO:24)

LHGDKVSFFC<u>KNKEKKCSY</u>TEDAQCIDGTI

G.  Deletion Mutant of Human Domain-5 of ApoH: (SEQ ID NO:25)

FKNGMLHGDKVSFFC<u>KNKEKKCSY</u>TEDAQCIDGTIEVPKC

FIG. 6
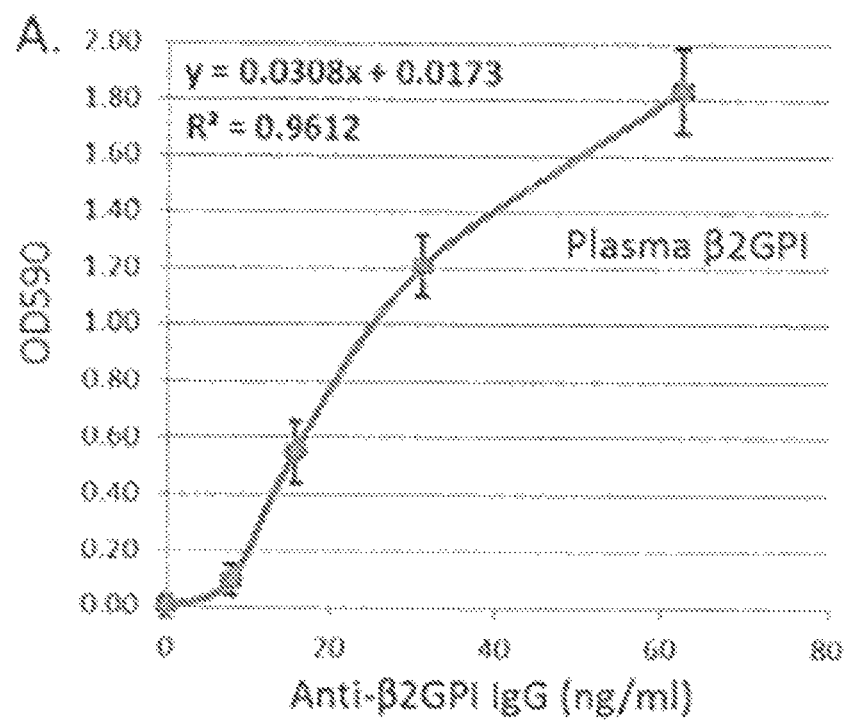
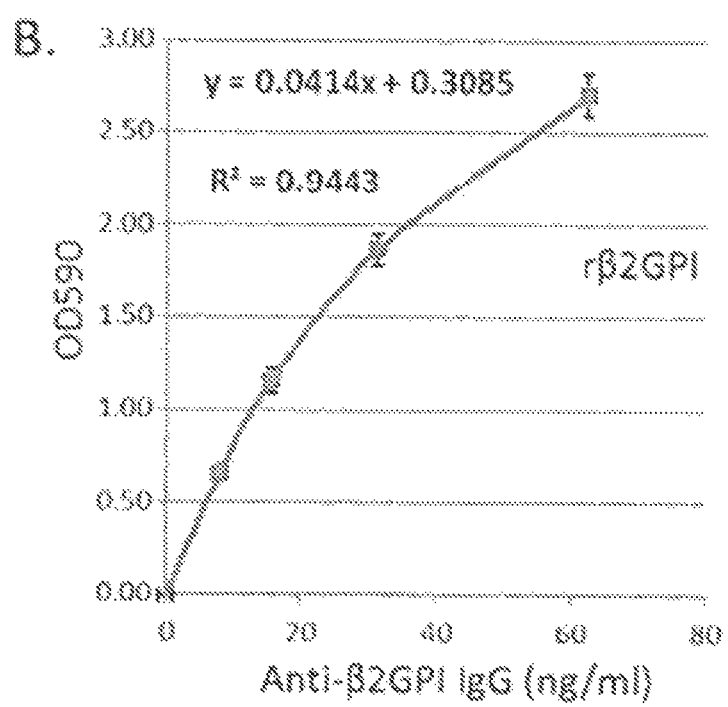

nAPOH = APOH cDNA with a native APOH signal peptide
spmAPOH = APOH cDNA with a signal peptide mutant

FIG. 9

| Human | 1 | M I S P V L I L F S S F L C H V A I A | 19 | (SEQ ID NO:6) |
| Chimpanzee | 1 | M I S P V L I L F S S F L C H V A I A | 19 | (SEQ ID NO:8) |
| Rhesus Monkey | 1 | M I S P V L I L F S S F L C H V A I A | 19 | (SEQ ID NO:9) |
| Gorilla | 1 | M I S P V L I L F S S F L C H V A I A | 19 | (SEQ ID NO:10) |
| Horse | 1 | M I S P V L I L F S S F L C H V A I A | 19 | (SEQ ID NO:11) |
| Mouse | 1 | M V S P V L A L F S A F L C H V A I A | 19 | (SEQ ID NO:12) |
| Rat | 1 | M I S P A L I F F S A F L C H V A I A | 19 | (SEQ ID NO:13) |
| Bovine | 1 | M L P P A L V L L L G F L C H V A I A | 19 | (SEQ ID NO:14) |

FIG. 11
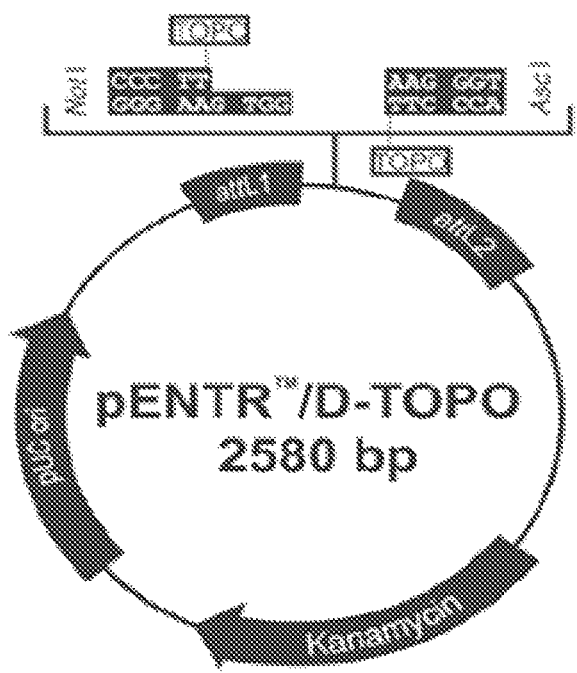
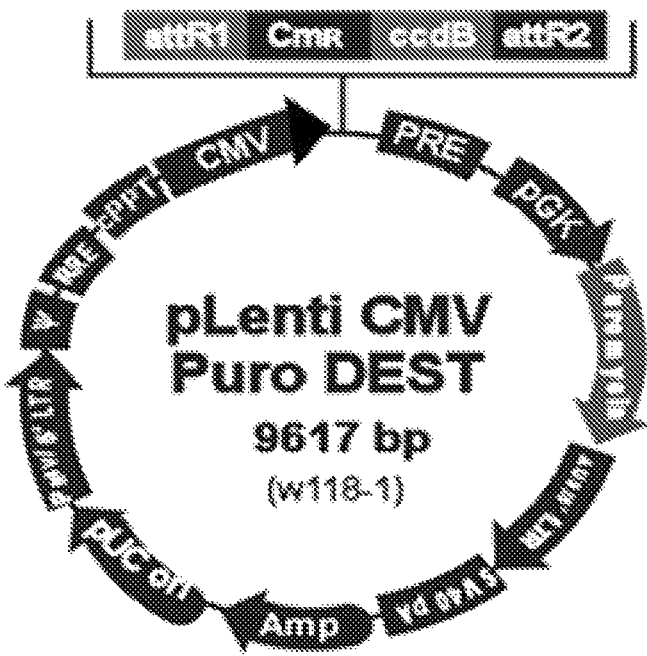

Overview of an exemplary anti-β2GPI-ELISA

Amino acid sequence of each domain of native human APOH

Domain-1: length 61 amino acids (SEQ ID NO:3)

RTCPKPDDLPFSTVVPLKTFYEPGEEITYSCKPGYVS<u>RGGMR</u>KFICPLTGLWPINTLKCTP

Domain-2: length 58 amino acids (SEQ ID NO:26)

RVCPFAGILENGAVRYTTFEYPNTISFSCNTGFYLNGADSAKCTEEGKWSPELPVCAP

Domain-3: length 63 amino acids (SEQ ID NO:27)

IICPPPSIPTFATLRVYKPSAGNNSLYRDTAVFECLPQHAMFGNDTITCTTHGNWTKLPECRE

Domain-4: length 60 amino acids (SEQ ID NO:28)

VKCPFPSRPDNGFVNYPAKPTLYYKDKATFGCHDGYSLDGPEEIECTKLGNWSAMPSCKA

Domain-5: length 83 amino acids (SEQ ID NO:29)

SCKVPVKKATVVYQGERVKIQEKFKNGMLHGDKVSFFCKNKEKKCSYTEDAQCIDGTIEVPKCF
KEHSSLAFWKTDASDVKPC

HUMAN β2-GLYCOPROTEIN I EXPRESSION

The present application claims priority to U.S. Provisional application Ser. No. 62/540,663, filed Aug. 3, 2017, which is herein incorporated by reference in its entirety.

STATEMENT REGARDING FEDERAL FUNDING

This invention was made with government support under grant number HL123098 awarded by the National Institutes of Health. The government has certain rights in the invention.

FIELD

Provided herein are compositions, systems, kits, and methods for expressing a peptide of interest, such as Apolipoprotein H (ApoH), also known as β2-glycoprotein I (β2GPI), at increased levels using a non-ApoH signal peptide (e.g., a signal peptide that permits increased protein export from cells). Also provided herein are compositions, systems, kits, and methods for employing such recombinant ApoH with a non-ApoH signal peptide to detect subject Apolipoprotein H antibodies in a sample from a subject (e.g., to diagnose antiphospholipid syndrome in a subject).

BACKGROUND

β2GPI (also known as ApoH) is the antigen toward which pathogenic antibodies are directed in patients with antiphospholipid antibody syndrome (APS), and solid-phase assays to measure such antibodies are used in diagnostic laboratories worldwide. These assays employ plasma β2GPI, which is difficult to purify and may become oxidized and denatured during standard purification procedures.

Antiphospholipid syndrome is the most common cause of acquired thrombophilia and a major cause of vascular morbidity and mortality. APS is defined by the development of arterial and venous thrombosis, or recurrent fetal loss, in patients with antiphospholipid antibodies (APLA). APLA are diagnosed in clinical laboratories by either clot-based assays (these antibodies are termed lupus anticoagulants), or solid-phase assays. The latter include ELISAs for anticardiolipin antibodies (ACL) or anti-β2GPI antibodies. The term "antiphospholipid" is a misnomer, since the initial description of these pathologic antibodies described their reactivity with anionic phospholipid and cardiolipin while subsequent studies demonstrated that the majority of APLA associated with APS are actually directed against β2GPI, a phospholipid binding protein. In the anticardiolipin assay, microplates are coated with cardiolipin, blocked with bovine serum, and then exposed to human test plasma; pathogenic antibodies within the plasma bind cardiolipin-bound β2GPI. In the anti-β2GPI ELISA, in general, plasma is incubated directly on β2GPI-coated plates and antibody binding assessed. The lupus anticoagulant test and anti-β2GPI ELISA have the strongest associations with thrombosis. Positivity in more than one test increases the risk of subsequent thrombosis.

While there are several anti-β2GPI assays on the market, all of these use purified plasma β2GPI. Purification of β2GPI from plasma is difficult, and most procedures utilize a perchloric acid precipitation step which may oxidize and cause conformational alterations in β2GPI that affect its antigenicity. These problems may underlie, at least in part, the observation that inter-laboratory reproducibility of the anti-β2GPI ELISA is poor. Recombinant β2GPI (rβ2GPI) has been difficult to produce due to its complex conformation and many disulfide bonds.

SUMMARY

Provided herein are compositions, systems, kits, and methods for expressing a peptide of interest, such as Apolipoprotein H (ApoH), also known as β2-glycoprotein I (β2GPI), at increased levels using a non-ApoH signal peptide (e.g., a signal peptide that permits increased protein export from cells). Also provided herein are compositions, systems, kits, and methods for employing such recombinant ApoH with a non-ApoH signal peptide to detect subject Apolipoprotein H antibodies in a sample from a subject (e.g., to diagnose antiphospholipid syndrome in a subject).

In some embodiments, provided herein are compositions comprising: a non-natural peptide, or nucleic acid sequence encoding said non-natural peptide, wherein said non-natural peptide comprises: a) a signal peptide portion comprising, or consisting of, a hydrophobic region comprising at least seven consecutive hydrophobic amino acids (e.g., comprising or consisting of 7-14 consecutive hydrophobic amino acids; e.g., 7, 8, 9, 10, 11, 12, 13, or 14 consecutive hydrophobic amino acids), and b) a peptide of interest portion. In certain embodiments, the peptide of interest portion comprises a protein selected from: a therapeutic protein, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, an extracellular domain of a cell surface receptor or a fragment thereof, an enzyme, a zymogen, an enzyme inhibitor, a coagulation factor, or protein with enzymatic activity. In particular embodiments, the peptide of interest portion comprises at least a portion of human Apolipoprotein H. In other embodiments, the peptide of interest portion is able to specifically bind to anti-Apolipoprotein H antibodies (anti-β2-glycoprotein-I antibodies). In further embodiments, the peptide of interest portion comprises, or consists of, at least a portion of Domain I of human Apolipoprotein H (ApoH).

In certain embodiments, the signal peptide comprises, or consists of, i) the hydrophobic region, ii) a charged region that is N-terminal of the hydrophobic region, and iii) a neutral region that is C-terminal of the hydrophobic region. In certain embodiments, the non-natural peptide is between 12 and 500 total amino acids in length (e.g., 12 . . . 20 . . . 40 . . . 75 . . . 150 . . . 250 . . . 310 . . . 330 . . . 400 . . . 450 . . . or 500 amino acids in length).

In certain embodiments, provided herein are methods of expressing a non-natural peptide comprising: culturing a cell containing an expression vector encoding a non-natural peptide such the non-natural peptide is expressed in, and exported from, the cell, wherein the non-natural peptide comprises: a) a signal peptide portion comprising, or consisting of, a hydrophobic region comprising at least seven consecutive hydrophobic amino acids; and b) a peptide of interest portion.

In other embodiments, the methods further comprise: purifying the non-natural peptide that has been exported from the cell to generate a purified preparation. In other embodiments, the non-natural peptide is exported from the cell at a level that is at least two times greater (e.g., two times . . . three times . . . four times . . . five times . . . or ten times greater) than when the expression vector encoding human Apolipoprotein H with natural signal peptide (SEQ ID NO:1) is employed instead of the non-natural peptide under identical conditions.

In certain embodiments, provided herein are methods of detecting the presence or absence of anti-Apolipoprotein H antibodies (anti-β2-glycoprotein-I antibodies) in a sample comprising: a) contacting a sample with a non-natural peptide, wherein the non-natural peptide specifically binds anti-Apolipoprotein H antibodies, if present, to form a complex, wherein the non-natural peptide comprises: i) a signal peptide portion comprising, or consisting of, a hydrophobic region comprising at least seven consecutive hydrophobic amino acids (e.g., comprising or consisting of 7-14 consecutive hydrophobic amino acids); and ii) a peptide of interest portion, wherein the peptide of interest portion is able to specifically bind to anti-Apolipoprotein H antibodies (anti-β2-glycoprotein-I antibodies), and wherein the peptide of interest portion comprises, or consists of, at least a portion of Domain I of human Apolipoprotein H (ApoH) and/or at least a portion of Domain V of ApoH; and b) detecting the presence or absence of the complex in the sample. In some embodiments, the peptide of interest portion is able to specifically bind to anti-Apolipoprotein H antibodies from a patient with antiphospholipid syndrome. In certain embodiments, the signal peptide comprises, or consists of, i) the hydrophobic region, ii) a charged region that is N-terminal of the hydrophobic region, and iii) a neutral region that is C-terminal of the hydrophobic region.

In some embodiments, the detecting the presence or absence of the complex detects the presence of the complex, thereby indicating the presence of the anti-Apolipoprotein H antibodies in the sample. In further embodiments, the detecting the presence or absence of the complex detects the absence of the complex, thereby indicating the absence of the anti-Apolipoprotein H antibodies in the sample. In certain embodiments, the non-natural peptide comprises a label (e.g., detectable label and/or one that binds another moiety, such as on beads or other solid surface). In certain embodiments, the methods further comprise contacting the sample with a solid support comprising moieties that bind the label. In additional embodiments, the methods further comprise: incubating the sample under conditions such that: i) the non-natural peptide specifically binds the anti-Apolipoprotein H antibody to form a complex, and ii) the complex binds to the solid support via the label binding at least one of the moieties. In other embodiments, the methods further comprise washing the solid support. In some embodiments, the methods further comprise adding to the sample a detectably labeled secondary antibody capable of binding the Apolipoprotein H antibody in the complex. In certain embodiments, the sample is any biological sample that potentially contains pathological anti-ApoH antibodies. In some embodiments, the sample is selected from the group consisting of: a blood sample, a serum sample, a plasma sample, and a urine sample.

In certain embodiments, provided herein are methods of detecting antiphospholipid syndrome in a subject comprising: a) contacting a sample from a subject suspected of containing a subject antibody to Apolipoprotein H (β2GPI) with a non-natural peptide, wherein the non-natural peptide specifically binds the subject antibody to form a complex, wherein the non-natural peptide comprises: i) a signal peptide portion comprising, or consisting of, a hydrophobic region comprising at least seven consecutive hydrophobic amino acids (e.g., comprising or consisting of 7-14 consecutive hydrophobic amino acids); and ii) a peptide of interest portion, wherein the peptide of interest portion is able to specifically bind to anti-Apolipoprotein H antibodies (anti-β2-glycoprotein-I antibodies) from a patient with antiphospholipid syndrome, and wherein the peptide of interest portion comprises, or consists of, at least a portion of Domain I of human Apolipoprotein H (ApoH); and b) detecting the presence of the complex, thereby detecting the presence antiphospholipid syndrome in the subject. In certain embodiments, the signal peptide comprises, or consists of, i) the hydrophobic region, ii) a charged region that is N-terminal of the hydrophobic region, and iii) a neutral region that is C-terminal of the hydrophobic region.

In certain embodiments, provided herein are kits and systems comprising: a) composition comprising: a non-natural peptide, or nucleic acid sequence encoding the non-natural peptide, wherein the non-natural peptide comprises: i) a signal peptide portion comprising, or consisting of, a hydrophobic region comprising at least seven consecutive hydrophobic amino acids (e.g., comprising or consisting of 7-14 consecutive hydrophobic amino acids); and ii) a peptide of interest portion; and b) at least one of the following: i) cells, ii) a solid support, and iii) a detectable label. In certain embodiments, the signal peptide comprises, or consists of, i) the hydrophobic region, ii) a charged region that is N-terminal of the hydrophobic region, and iii) a neutral region that is C-terminal of the hydrophobic region.

In particular embodiments, provided herein are compositions comprising: a) a signal peptide comprising or consisting of, a hydrophobic region comprising at least seven consecutive hydrophobic amino acids (e.g., comprising or consisting of 7-14 consecutive hydrophobic amino acids); and b) a protein of interest portion, wherein the signal peptide is not attached to the peptide of interest portion.

In certain embodiments, the signal peptide comprises, or consists of, i) the hydrophobic region, ii) a charged region that is N-terminal of the hydrophobic region, and iii) a neutral region that is C-terminal of the hydrophobic region. In some embodiments, the charged region comprises at least two charged amino acids (e.g., 2, 3, 4 or more, consecutive or non-consecutive). In other embodiments, the neutral region comprises at least two neutral amino acids (e.g., 2, 3, 4 or more, consecutive or non-consecutive). In some embodiments, the Apolipoprotein H antibodies are from a patient with antiphospholipid syndrome.

In certain embodiments, the peptide of interest portion comprises the at least a portion of Domain I of human ApoH, and wherein the at least a portion of Domain I of human ApoH comprises peptide sequence RGGMR (SEQ ID NO:30). In some embodiments, the peptide of interest portion comprises at the least a portion of Domain I of human ApoH, and wherein the at least a portion of Domain I of human ApoH comprises peptide selected from SEQ ID NOS:3, 4, 5, and 22. In other embodiments, the peptide of interest portion comprises the at least a portion of Domain V of human ApoH, and wherein the at least a portion of Domain V of human ApoH comprises peptide selected from SEQ ID NOS:23, 24, 25, and 29. In further embodiments, the peptide of interest portion comprises the at least a portion of Domain I of human ApoH, and wherein the at least a portion of Domain I of human ApoH comprises the entire Domain I of human ApoH (SEQ ID NO:3) or SEQ ID NO:3 with one, two, or three conservative amino acid changes. In certain embodiments, the peptide of interest portion comprises, or consists of: i) the human apolipoprotein H protein shown in SEQ ID NO:2 or 2) the protein shown in SEQ ID NO:2 with one, two, or three conservative amino acid changes. In further embodiments, the hydrophobic region comprises between eight and fifteen consecutive hydrophobic amino acids. In other embodiments, the at least seven hydrophobic amino acids are each independently selected from the group consisting of: alanine, valine, leucine, isoleucine, proline, phenylalanine, trypophane, cysteine and methionine. In additional embodiments, the at least seven hydrophobic amino acids are each independently selected from the group consisting of: leucine, valine, proline, and trypophane. In particular embodiments, the hydrophobic region comprises at least seven consecutive amino acids from LLLWVLLLVWP (SEQ ID NO:31). In further embodiments, the hydrophobic region does not contain any non-hydrophobic amino acids. In other embodiments, the hydrophobic region contains only hydrophobic amino acids. In certain embodiments, the signal peptide comprises, or consists of, one of the following amino acid sequences: a) METDTLLLWVLLLLWVPGST (SEQ ID NO:32); b) METDTLLLWVLLLLWVPGS (SEQ ID NO:33); c) METDTLLLWVLLLLWVPG (SEQ ID NO:34); d) METDTLLLWVLLLLWVP (SEQ ID NO:35); and e) METDTLLLWVLLLW (SEQ ID NO:36).

In some embodiments, the signal peptide portion comprises a methionine N-terminal of the charged region. In certain embodiments, the charged region is two to four amino acids in length. In other embodiments, the charged region comprises or consists of three or four charged amino acids. In some embodiments, the charged regions further comprises at least one neural-polar amino acid. In particular embodiments, the at least two charged amino acids are aspartic acid and glutamic acid. In other embodiments, the at least two charged amino acids are independently selected from: lysine, arginine, histidine, aspartic acid and glutamic acid. In further embodiments, the neutral region comprises or consisting of three neutral amino acids. In certain embodiments, the at least two neutral amino acids comprises two or three neutral-polar amino acids. In other embodiments, the at least two neutral amino acid comprises, or consists of, one neutral-nonpolar amino acid and at least one neutral-polar amino acid. In other embodiments, the at least one neutral-nonpolar amino acid is glycine. In particular embodiments, the at least one neutral-polar amino acid is selected from serine and threonine. In further embodiments, the non-natural peptide further comprises c) a cleavage site, wherein the cleavage site is located between the signal peptide portion and the peptide of interest portion.

In some embodiments, provided herein are composition, systems, and kits, comprising a non-natural peptide, wherein said non-natural peptide comprises a signal peptide, and wherein said signal peptide comprises, or consists of, one of the following amino acid sequences: a) METDTLLL-WVLLLLWVPGST (SEQ ID NO:32); b) ETDTLLL-WVLLLLWVPGST (SEQ ID NO:33); c) TDTLLLWVLLL-WVPGST (SEQ ID NO:34); d) DTLLLWVLLLLWVPGST (SEQ ID NO:35); and e) TLLLWVLLLLWVPGST (SEQ ID NO:36). In certain embodiments, the non-natural peptide further comprises a peptide of interest that is linked to said signal peptide. In certain embodiments, the peptide of interest comprises at least a portion of human Apolipoprotein H or another protein that is known in the art to be expressed recombinantly in vitro. Such proteins of interest include therapeutic proteins and research regents and are well known in the art (e.g., and can be readily found on PubMed and in the patent literature). Certain proteins of interest include proteins that are currently considered difficult to express in vitro.

DESCRIPTION OF THE FIGURES

FIG. 1A shows the human Apolipoprotein H (ApoH) amino acid sequence (SEQ ID NO:1) with the signal peptide underlined. FIG. 1B shows the human ApoH amino acid sequence without the signal peptide (SEQ ID NO:2).

FIG. 2 shows: A) the amino acid sequence of native human Domain-1 of ApoH: (SEQ ID NO:3); B) an exemplary thirteen amino acid deletion mutant of human Domain-1 of ApoH (SEQ ID NO:4); C) an exemplary fifteen amino acid deletion mutant of human Domain-1 of ApoH (SEQ ID NO:5); D) an exemplary twenty-five amino acid deletion mutant of human Domain-1 of ApoH (SEQ ID NO:22); E) an exemplary twenty amino acid deletion mutant of human Domain-5 of ApoH (SEQ ID NO:23); F) an exemplary thirty amino acid deletion mutant of human Domain-5 of ApoH (SEQ ID NO:24); and G) an exemplary forty amino acid deletion mutant of human Domain-5 of ApoH (SEQ ID NO:25).

FIG. 6 shows high binding polystyrene plates coated with 2 μg/ml natural (A) or rβ2GPI (B) then incubated with increasing concentrations of affinity-purified rabbit anti-β2GPI IgG. Binding was detected using a peroxidase-conjugated goat anti-human IgG. rβ2GPI was detected at lower antibody concentrations with a steeper binding curve than natural β2GPI.

FIG. 9: Alignment of the APOH native signal peptide from different species.

FIG. 11: Vector maps of cloning vectors used A) pENTR/D-TOPO entry vector and B) pLenti CMV Puro DEST lentiviral destination vector.

FIG. 15: Binding of anti-β2GPI antibodies from patient 21 (APS-21) to rβ2GPI-WT and rβ2GPI-SEGVG (SEQ ID NO:37). The graph on the left depicts binding of total affinity-purified immunoglobulin, while that on the right shows binding of affinity-purified IgG only.

FIG. 21 shows the amino acid sequence of each domain of native human APOH.

DETAILED DESCRIPTION

Figure 3:
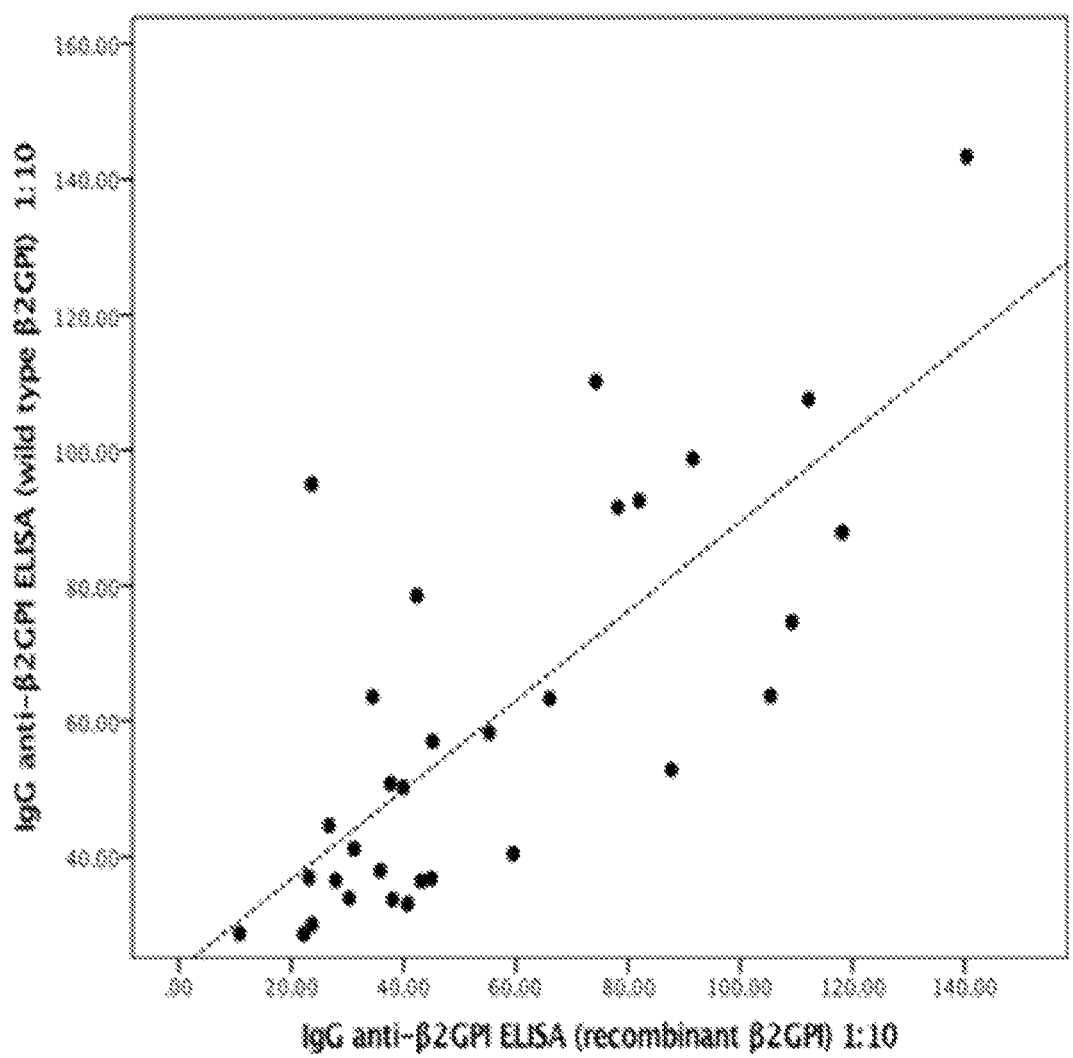
FIG. 3 shows the correlation between anti-β2GPI IgG ELISA using (A) recombinant, and (B) wild-type ApoH (β2GPI) as a Cofactor.
Figure 3:
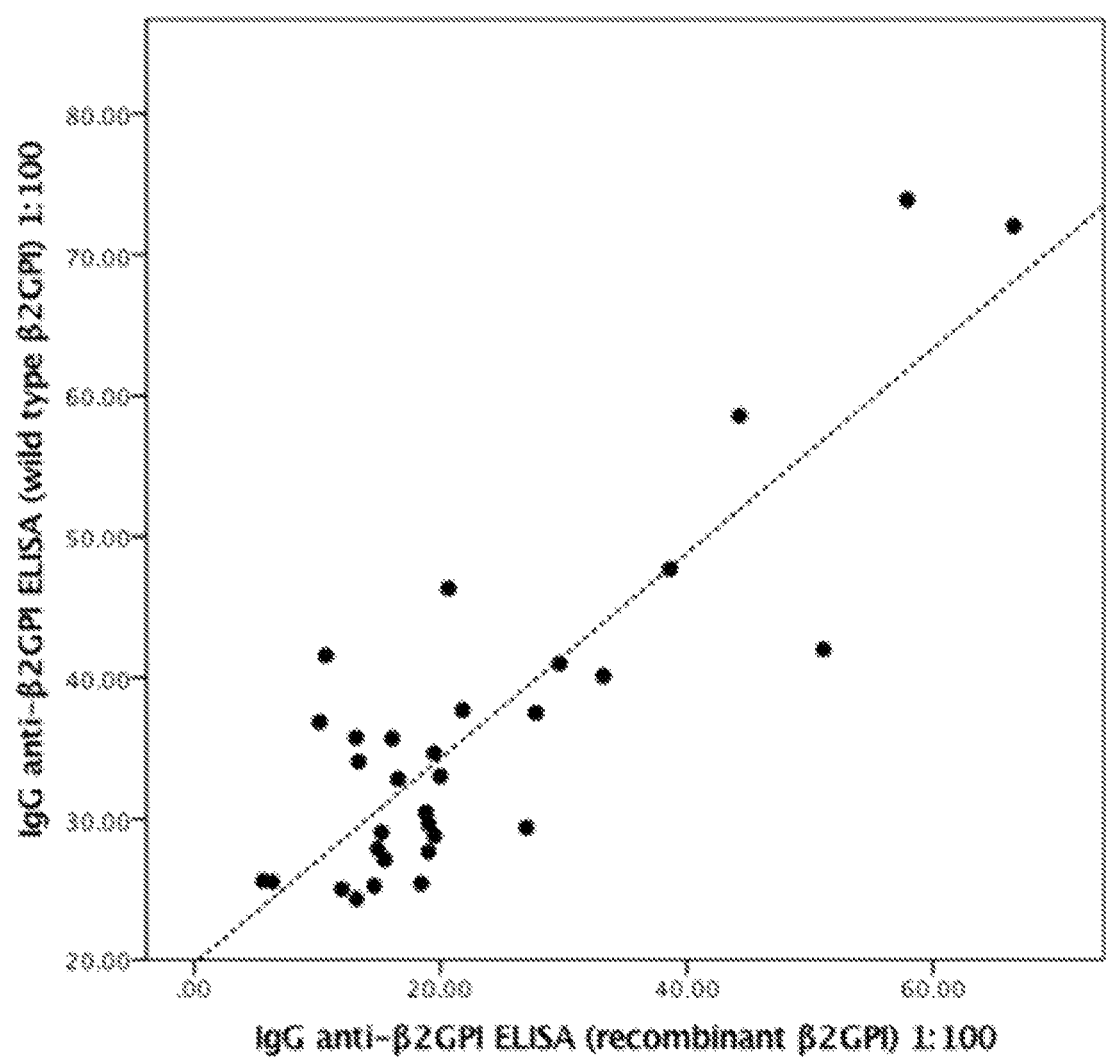

Provided herein are compositions, systems, kits, and methods for expressing a peptide of interest, such as Apolipoprotein H (ApoH), also known as β2-glycoprotein I (β2GPI), at increased levels using a non-ApoH signal peptide (e.g., a signal peptide that permits increased protein export from cells). Also provided herein are compositions, systems, kits, and methods for employing such recombinant ApoH with a non-ApoH signal peptide to detect subject Apolipoprotein H antibodies in a sample from a subject (e.g., to diagnose antiphospholipid syndrome in a subject).

Each of peptides shown in SEQ ID NOS:2-5, 7, 22-29, and 32-36 may be constructed with longer, shorter, or mutated versions thereof. For example, one could change one, two, three amino acids in these sequences. For example, one could make conservative changes to such amino acid sequences. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine. In certain embodiments, provided herein are peptides that have substantial identity (e.g., at least 95% identity) to the amino acid sequences shown in SEQ ID Nos:2-5, 7, 22-29, and 32-36. In certain embodiments, the following hydrophobic amino acids may be substituted for each other: glycine (Gly), alanine (Ala), valine (Val), leucine (Leu), isoleucine (Ile), proline (Pro), phenylalanine (Phe), methionine (Met), and tryptophan (Trp). In some embodiments, the following charged amino acids may be substituted for each other: Aspartic acid (Asp), Glutamic acid (Glu), Lysine (Lys), Arginine (Arg), and Histidine (His). In particular embodiments, the following positive-polar amino acids may be substituted for each other: Lysine (Lys), Arginine (Arg), and Histidine (His). In other embodiments, the following neutral-polar amino acids may be substituted for each other: Tyrosine (Tyr), Serine (Thr), Threonine (Thr), Asparagine (Asn), Glutamine (Gln), and Cysteine (Cys). In some embodiments, the following neutral-nonpolar amino acids may be substituted for each other: alanine (Ala), glycine (Gly), isoleucine (Ile), leucine (Leu), methionine (Met), phenylalanine (Phe), proline (Pro), and valine (Val).

Current anti-β2GPI assays use plasma-derived β2GPI as the target for measuring anti-β2GPI antibodies. This approach has many shortcomings, including: 1) the use of human plasma to obtain the protein, 2) the use of harsh conditions (perchloric acid precipitation, etc.) to isolate β2GPI, which results in protein oxidation and loss of conformation, 3) the time and expense required to obtain plasma, isolate and characterize the protein, and 4) potential impurities in a preparation of protein obtained from plasma. In contrast, the methods and compositions described herein have produced rβ2GPI with yields of >20 mg/liter, with only a gentle, heparin-sepharose purification step to isolate the protein from media (see Examples below). Overall, we estimate the cost of obtaining the recombinant protein to be approximately ⅕ of that required to obtain the protein from plasma.

In addition, several studies have demonstrated that anti-β2GPI antibodies reactive with domain 1 of β2GPI are more pathogenic that those against other parts of the proteins. Identification of such antibodies in patients will improve the ability to identify patients at highest risk of primary or recurrent thrombosis, as well as pregnancy loss. While a clinical assay (Innova) currently exists that measures antibodies to domain 1, this assay does not use intact β2GPI as a target.

The expression systems described herein allows for production of multiple forms of rβ2GPI including small versions of the protein such as isolated domain 1 (or other domains), domain deletion mutants or polypeptides containing scrambled domains or even pieces of other proteins substituted for specific β2GPI domains. Since each of the 5 domains of β2GPI is a "sushi" domain, a module present in many different proteins, one can swap in a related but non-homologous domain for any domain within β2GPI thought to be important to its function. Some examples of proteins that contain sushi domains include selectins, complement regulatory proteins, tissue factor pathway inhibitor, IL2-receptor, and many others. Specific substitutions would focus on domain 1, which contains the β2GPI epitope, domain 5, which is thought to mediate β2GPI binding to cells, and potentially other domains as well.

The use of a recombinant proteins containing at least part of domain 1 of human ApoH as a "decoy" for anti-β2GPI antibodies in patients with APS could be used for treatment. While not limited to any particular mechanism, it is believed that anti-β2GPI antibodies induce vascular activation by binding to cell-bound β2GPI domain 1 that is anchored to cells via binding through domain 5. Thus, free domain 1 (or fragments thereof) may bind anti-β2GPI antibodies, preventing them from binding cell bound β2GPI. Likewise, recombinant β2GPI domain 5 may inhibit the binding of β2GPI to cells.

The β2GPI peptides produced by the methods described herein may be used in any type of suitable immunoassay. The present description is not limited by the type of immunoassay employed to detect patient antibodies in a sample. A number of exemplary formats are as follows. In an indirect assay, β2GPI peptide or protein is coated on solid phase (e.g., beads) and then contacted with a sample (e.g. 18 minutes), followed by a wash step. Then, in a second step, patient antibodies to β2GPI are detected by contacting the immune complex with labeled "second" antibody to detect human IgG (or IgM) bound to the solid phase (e.g. for 4 minutes). Another assay is a two-step direct (sandwich) assay. In this assay, β2GPI peptide or protein is coated on solid phase (e.g., beads) and contacted with sample (e.g. for about 18 minutes) and then washed. In a second step, antibodies to β2GPI are detected with a labeled β2GPI peptide/protein that binds to human IgG (or IgM) bound to the solid phase containing the β2GPI protein (e.g. for 4 minutes). A one-step direct (sandwich) assay could also be employed. In such an assay, β2GPI peptide or protein is coated on solid phase and contacted with sample (e.g., for about 18 minutes) and with labeled β2GPI peptide/protein at the same time or about the same time (e.g., for 18 minutes). Another type of assay is a solution phase capture. In such an assay, the sample is contacted with both protein tagged β2GPI peptide or protein (e.g., biotin tag, FLAG-tag, HA-tag, etc.) and labeled β2GPI peptide or protein in the presence of a solid phase coated with an affinity molecule (e.g., streptavidin or protein tag antibody). If the patient antibodies are present in the sample, the tagged peptide or protein and labeled β2GPI peptides or proteins can bind to patient antibodies in a complex that can be captured by the associated protein tag to a solid phase support. In all of these assay formats, the solid phase is further processed to elicit a signal from labeled β2GPI associated with patient antibodies and with the solid phase. Since the literature suggests that there exist lupus anticoagulants, detected using functional clotting assays that depend on either β2GPI or prothrombin for their activity, and that the β2GPI-dependent lupus anticoagulants are most important in predicting APS clinical events, the recombinant proteins described herein could also be used for more predictive clotting assays.

Notably, the β2GPI proteins are labeled with a detectable label or labeled with a specific partner that allows capture or detection. For example, the labels may be a detectable label, such as a fluorophore, radioactive moiety, enzyme, biotin/avidin label, chromophore, chemiluminescent label, or the like. Still further the invention contemplates the preparation of β2GPI diagnostic kits comprising the immunodiagnostic reagents described herein and instructions for the use of the immunodiagnostic reagents in immunoassays for determining the presence of β2GPI antibodies.

The immunoassays may be packaged into a kit. Any secondary antibodies, which are provided in the kit, such as anti-IgG antibodies and anti-IgM antibodies, can also incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates. In certain immunoassays, there are two containers provided.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components. The various components of the kit optionally are provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In some embodiments, the detectable label is at least one acridinium compound. In such embodiments, the kit can comprise at least one acridinium-9carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the antigens for antibody detection may be detectably labeled, and any antibodies provided in kit for use along with such reagents also may be detectably labeled. If desired, the kit can contain a solid support phase, such as a magnetic particle, bead, test tube, microtiter plate, cuvette, membrane, scaffolding molecule, film, filter paper, disc or chip.

The present disclosure provides immunoassays and combination immunoassays method for determining the presence, amount or concentration of anti-β2GPI antibodies in a test sample. Any suitable assay known in the art can be used in such methods. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA)(e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc.

Any suitable detectable label as is known in the art can be used as anyone or more of the detectable labels. For example, the detectable label can be a radioactive label (such as 3H, 125I, 35S, 14C, 32p, and 33p), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmiumselenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 39173921 (2004); and Adamczyk et al., Org. Lett. 5: 3779-3782 (2003)).

EXAMPLES

Example 1

β2-glycoprotein I (β2GPI), also known as Apolipoprotein H (ApoH), is the primary antigen for antiphospholipid antibodies (Ab), and Ab to β2GPI are associated with thrombosis and recurrent fetal loss. β2GPI is comprised of 5 "sushi" domains. Complex disulfide bonding renders β2GPI a challenging protein to produce recombinantly in high yield and most studies have utilized domain-deletion mutants produced on a lab scale for structure-function analyses. β2GPI also has a complex tertiary structure, and is reported to circulate in a "circular" form that may "open" to expose the antigenic site for β2GPI Ab under specific conditions. This Examples describes new methods to produce recombinant β2GPI in which replacement of the leader (signal) peptide allows large scale expression using a lentiviral system with one-step purification on heparin-sepharose. The ability of this protein to bind anti-β2GPI Ab was compared with that of plasma-derived (wild type, WT) β2GPI.

Methods

β2GPI cDNA was cloned into pLenti CMV DEST. The β2GPI containing vector was used to transduce HEK293 cells with selection using puromycin. β2GPI was purified from conditioned medium using HiTrap Heparin HP. Plasma β2GPI was purified using a protocol employing perchloric acid precipitation followed by heparinsepharose and Mono-S chromatography.

To measure anti-β2GPI Ab, we analyzed plasma from 32 patients referred to the Cleveland Clinic Special Coagulation Laboratory for anti-β2GPI testing using the Inova Quanta-Lite ELISA. Normal plasma samples (n=15) were also analyzed at 1:100 dilution to determine cutoffs for anti-β2GPI positivity. Briefly, 96-well plates were coated overnight at 4° C. with 2 ug/ml WT or recombinant β2GPI. After blocking β2GPI-coated plates with BSA, 50 ul of patient plasma at 1:10 and 1:100 dilutions were added to individual wells in quadruplicate. A standard curve for IgG binding to each plate was created using affinity-purified rabbit anti-β2GPI IgG at concentrations of 15, 31.25, 62.5, 125, and 250 ng/ml. After incubation for 30 minutes at room temperature, plates were washed three times and 100 ul of a 1:5000 dilution of goat anti-human IgG was added. After 30 minutes, wells were again washed prior to adding 100 ul/well of a-phenylenediamine dihydrochloride. Plates were read at 490 nm after 15 minutes following addition of 25 ul/well $H_2SO_4$. Results from different plates were standardized by extrapolating the amount of bound Ab from the standard curve prepared on each plate.

To compare performance of recombinant β2GPI against WT β2GPI in ELISA we first evaluated correlation using recombinant and WT β2GPI by Spearman's test. The two sets of ELISAs were also compared using the Wilcoxon matched pairs test. ELISA readings were considered positive if they were >90th percentile on a curve established using 15 normal plasmas. Sensitivity and specificity of the assays was determined with respect to the results of the clinical assay.

Results

Figure 4:
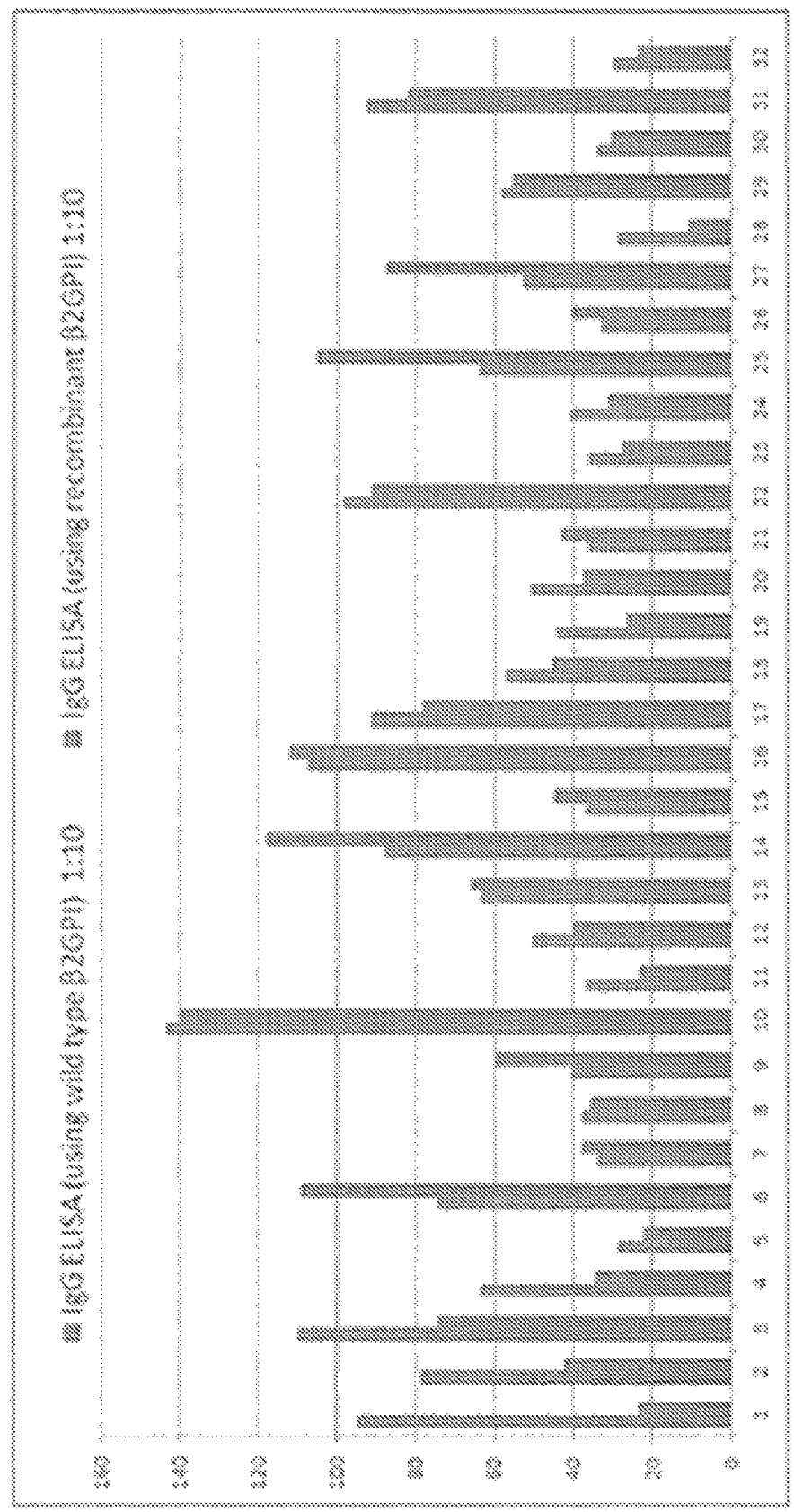
FIG. 4 shows a comparison of IgG anti-β2GPI antibody levels in plasma from 32 patients using wild type and recombinant β2GPI at 1:10 dilution. Using the Wilcoxon rank sum test for paired sample, there was no significant difference between results of the ELISA using wild-type or recombinant β2GPI (mean difference 4.26±22.25, P<0.001).

Recombinant β2GPI was produced in high yield (10-20 mg/L) and purified to homogeneity with a single heparin chromatography step. The purified protein migrated as a single band of 50 kD on SDS-PAGE with a characteristic increase in $M_r$ upon reduction. Anti-β2GPI IgG ELISA using WT and recombinant β2GPI demonstrated excellent correlation at both 1:10 (Spearman's rho 0.70, P<0.001) and 1:100 dilution (Spearman rho 0.727, p<0.001) (FIG. 3). Using the Wilcoxon test for paired samples, there was no significant difference between results of the ELISA using WT or recombinant β2GPI at 1:10 dilution (mean difference 4.26±22.25, P<0.001) and a small difference at 1:100 dilution (mean difference 13.51±7.59, P<0.001) (FIG. 4). Of the 32 patient samples, 6 were known positive for anti-β2GPI IgG (titer~20 GPL). Using a 90th percentile cutoff established using healthy volunteer samples, the ELISA using recombinant β2GPI correctly identified 6/6 positive samples (sensitivity 100%). The ELISA using plasma-derived β2GPI correctly identified 5/6 positive samples (sensitivity 83.3%, specificity 84%).

This Example demonstrates that recombinant β2GPI can be produced in high yield by this method and purified with a single heparin chromatography step. It is recognized by anti-β2GPI Ab at least as well as WT β2GPI.

Example 2

This Example describes a method of recombinant β2GPI (rβ2GPI) production that yields approximately 20 mg/liter of protein at low cost. This recombinant protein may be purified by a single heparin affinity-chromatography step, avoiding the harsh conditions needed to purify β2GPI from plasma. Initial works indicates that we can also produce rβ2GPI in which important antigenic sites recognized by pathogenic antibodies have been changed by site-directed mutagenesis. The use of rβ2GPI allows superior standardization and reproducibility compared to plasma β2GPI since the properties of the latter may be affected by purification methods, altered glycosylation among plasma donors, and other variables.

Figure 5:
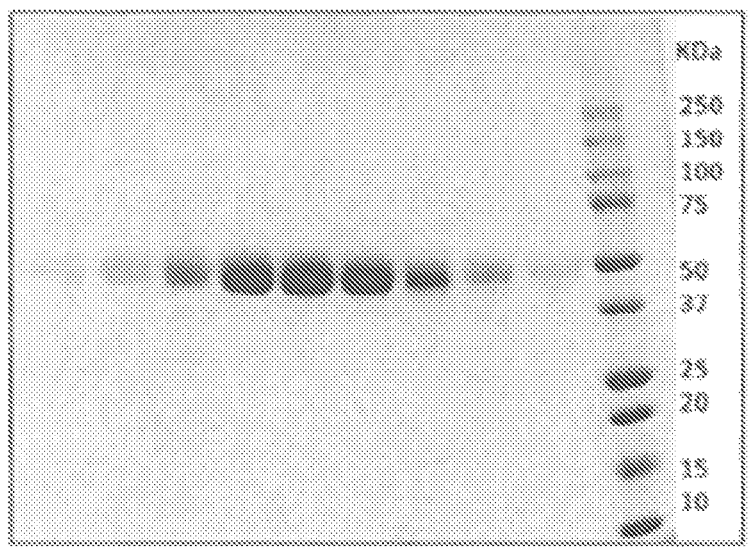
FIG. 5 depicts an SDSPAGE analysis of rβ2GPI within fractions eluted from a heparin-superose column by increasing concentrations of salt at neutral pH. Pure protein is obtained with single step purification.

We have developed a new strategy for production of rβ2GPI in human cells. This product could largely replace plasma-derived β2GPI in clinical ELISAs. Moreover, there is also an undeveloped market for the sale of β2GPI, which is used for research purposes, as well as development of additional clinical assays such as measurement of β2GPI-dependent lupus anticoagulants. The technology is ready for immediate use.

β2GPI was produced in mammalian cells and purified using single step heparin-superose chromatography. Yield of 10-20 mg/liter are routinely obtained, though purification conditions could be further optimized. FIG. 5 depicts an SDS-PAGE analysis of rβ2GPI within fractions eluted from a heparin-superose column by increasing concentrations of salt at neutral pH. Pure protein is obtained with single step purification.

To determine whether rβ2GPI is recognized by anti-β2GPI antibodies, we immunized rabbits with purified, human plasma β2GPI and affinity purified IgG on the same material. We then compared the ability of these purified rabbit antihuman anti-β2GPI antibodies to bind natural and rβ2GPI in a linear, concentration-dependent manner. As shown in FIG. 6, these antibodies bind both proteins. However, the affinity of the antibodies for rβ2GPI was significantly higher, as judged by the slope of the binding curves. Moreover, rβ2GPI was bound at lower concentrations by the antibodies. These results suggest that antigen preservation may be better on rβ2GPI compared to natural.

Finally, we tested the binding of IgG from 5 serum samples from patients with anti-β2GPI antibodies and 5 normal, healthy controls without such antibodies to ELISA plates coated with natural or recombinant β2GPI. In all cases, samples were tested at 1:5, 1:10 and 1:100 dilutions using standard procedures. Binding activity of IgG from the samples was converted to ng/ml of anti-β2GPI using the rabbit anti-β2GPI-derived standard curve after correction for sample dilution. The results of these studies are shown in Table 1.

TABLE 1

ELISA of normal and patient sera for antibodies to plasma or β2GPI

| | Serum dilution | 1:5 | 1:10 | 1:100 |
|---|---|---|---|---|
| Anti-β2GPI level (ng/ml) [Plasma β2GPI/recombinant β2GPI coating] | APS-1 | 394 | 709 | 3069 |
| | | 328 | 675 | 5439 |
| | APS-2 | 3 | 1 | ND |
| | | 126 | 295 | 484 |
| | APS-3 | 36 | 210 | ND |
| | | 98 | 147 | 154 |
| | APS-8 | 9 | 81 | 97 |
| | | 69 | 82 | ND |
| | APS-18 | 156 | 229 | 191 |
| | | 237 | 440 | 1852 |
| | N-27 | 21 | 28 | 163 |
| | | 37 | ND | |
| | N-28 | ND | | |
| | | ND | | |
| | N-29 | ND | | |
| | | ND | | |
| | N-30 | ND | | |
| | | 101 | | |
| | N-31 | 41 | 7 | ND |
| | | 30 | ND | |

Review of this table demonstrates that greater amounts of β2GPI were detected in wells coated with recombinant β2GPI in 4 of 5 patient (APS) sera tested. The largest differences were observed at serum dilutions of 1:100, which are used in many commercially available ELISAs. Moreover, the background binding of IgG from normal controls (N) was generally equal or lower to recombinant β2GPI than to plasma β2GPI.

Taken together, these findings suggest that recombinant β2GPI is recognized at least as well, if not better, than anti-β2GPI antibodies. Moreover, this reagent offers consistency, reproducibility, and overall better options for standardization compared to plasma β2GPI. With the possibility of cost savings due to a much simpler production and purification scheme, we believe that recombinant β2GPI provides a new option for clinical anti-β2GPI antibody assays.

Example 3

APOH Expression, Characterization and Use as a Diagnostic and Investigative Tool in Patients with Antiphospholipid Antibody Syndrome This Example describes further characterization of ApoH expression systems (e.g., as described in the Examples above).

I. Cloning and Expression of APOH cDNA

A. APOH cDNA Containing a Native Signal Peptide is Expressed but not Secreted

Figure 7:
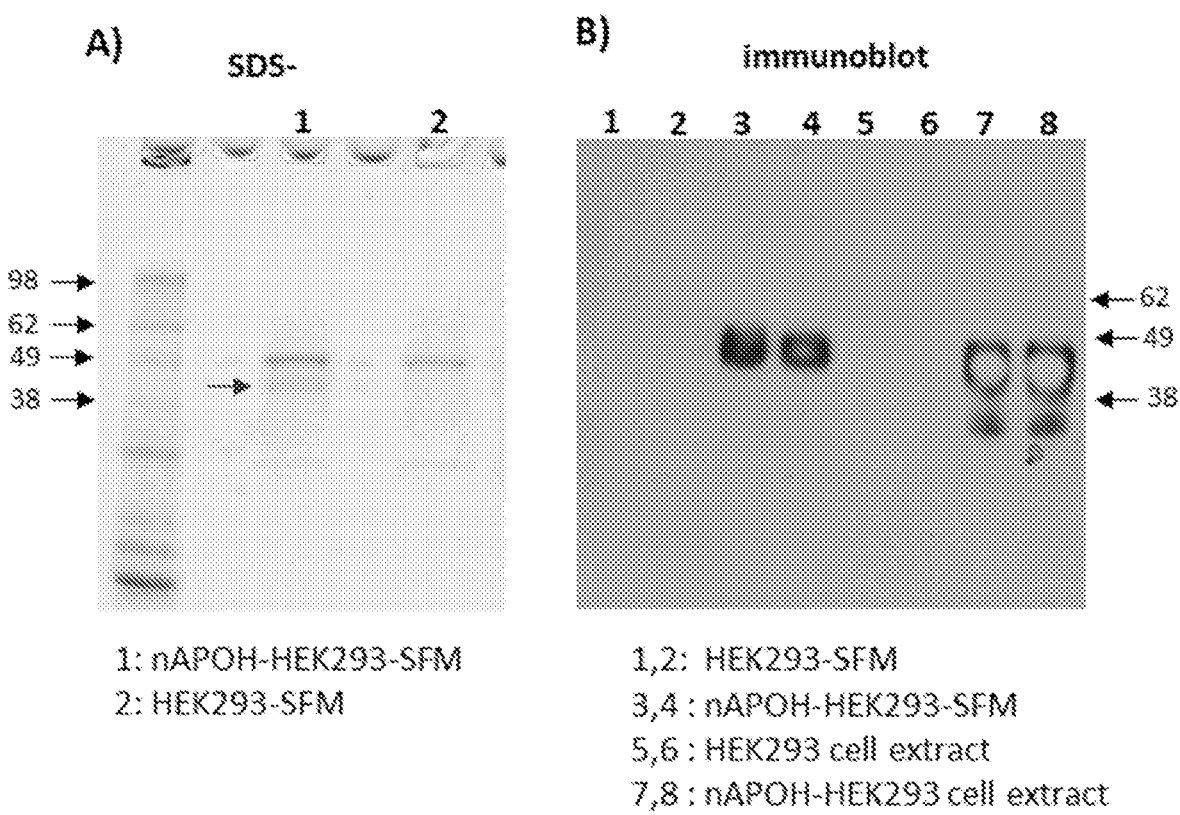
FIG. 7 shows an SDS-PAGE and immunoblot blot of serum-free medium (SFM) and cell extracts following transduction of HEK293 cells with lentivirus expressing nAPOH. A) SDS-PAGE and coomassie blue staining of SFM. Lane 1=SFM from nAPOH transduced 293 cells (nAPOH-HEK293) cells and control HEK293 cells not transduced with the lentiviral construct. A small amount of APOH is released into the SFM of nAPOH-HEK293 cells (arrow). (B) Immunoblot of SFM from non-transduced HEK293 cells (lanes 1 and 2, 5 and 6), lentivirus transduced nAPOH-HEK293 cells (lanes 3 and 4), and cell extracts from nAPOH-transduced HEK293 cells. The overexpressed bands observed in the immunoblots of cell extracts demonstrate sequestration of most of the protein within cells. These results demonstrate that the lentiviral-nAPOH construct induces robust expression of APOH, but that the expressed protein is not efficiently secreted.

Previous attempts to express APOH in bacterial and insect cell systems were unsuccessful. Therefore, the native APOH cDNA (containing the native signal peptide; see FIG. 1A), designated as nAPOH, was cloned into a lentiviral vector, and used to transduce HEK293 cells. We found that nAPOH was expressed in these cells, and though a small amount was secreted into the medium, the majority of the protein remained intracellular and was not secreted (FIG. 7).

B. Modification of the APOH Signal Peptide Leads to Efficient Secretion

Figure 8:
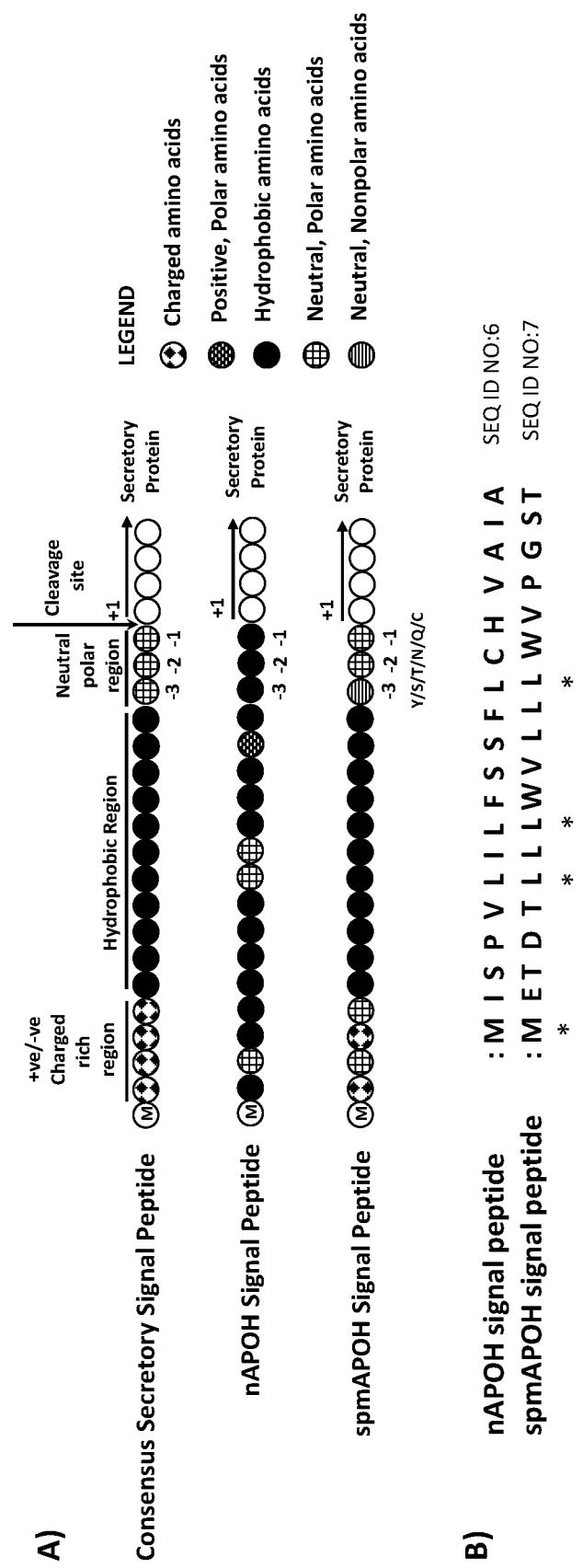
FIG. 8: Signal peptide sequences. A) Schematic sequences, by amino acid type, for a consensus signal peptide, the native APOH signal peptide, and spmAPOH signal peptide. B) Amino acid sequences of the native and spmAPOH signal peptides.

A known consensus sequence for a secretory signal peptide is characterized by the presence of three discrete regions within the peptide sequence (see, SAFC/Sigma Aldrich, Mascarenhas et al., Signal Peptide Optimization: Effect On Recombinant Monoclonal IgG Productivity, Product Quality And Antigen-Binding Affinity; 2009, herein incorporated by reference in its entirety). These include an N-terminal charged region of approximately 4 amino acids, a middle region containing 10-12 hydrophobic amino acids, and a C-terminal region of 3-4 polar amino acids with a net negative charge (see, FIG. 8A herein, and see FIG. 1 of Mascarenhas et al.). Review of the native APOH signal peptide sequence demonstrates significant homology with that of higher mammals, but deviates from the consensus sequence in several other species (FIGS. 8 and 9). We designed a signal peptide mutant APOH, which we designate as spmAPOH (FIG. 8B, SEQ ID NO:7), and assessed whether this improved APOH secretion.

C. Cloning of APOH cDNA into Lentiviral Vectors

Figure 10:
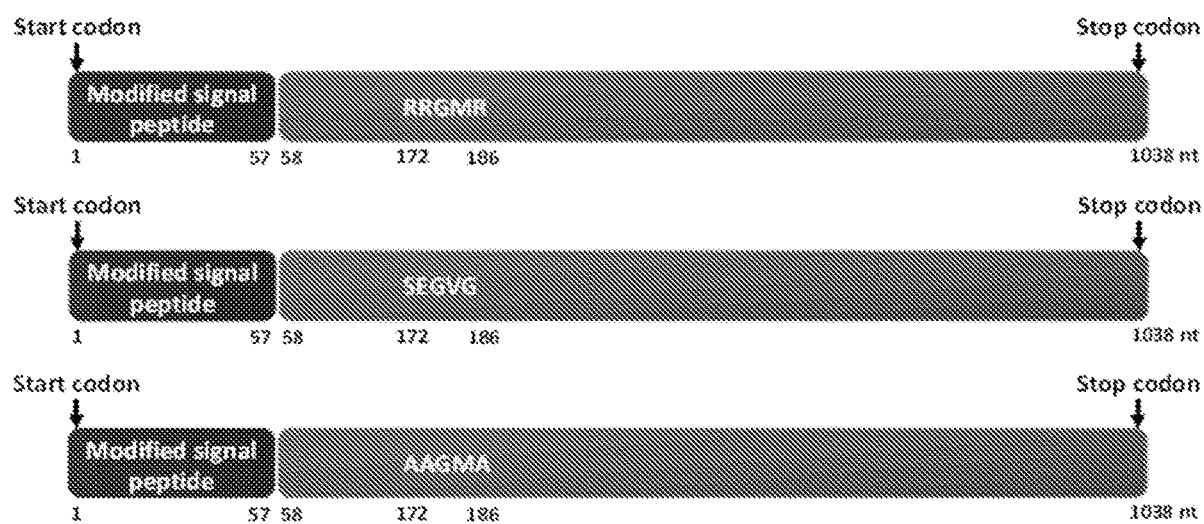
FIG. 10: APOH cDNA constructs A) spmAPOH-WT (RGGMR (SEQ ID NO:30) B) spmAPOH-mutant (SEGVG (SEQ ID NO:37)) and C) spmAPOH-mutant (AAGMA (SEQ ID NO:38)).
Figure 12:
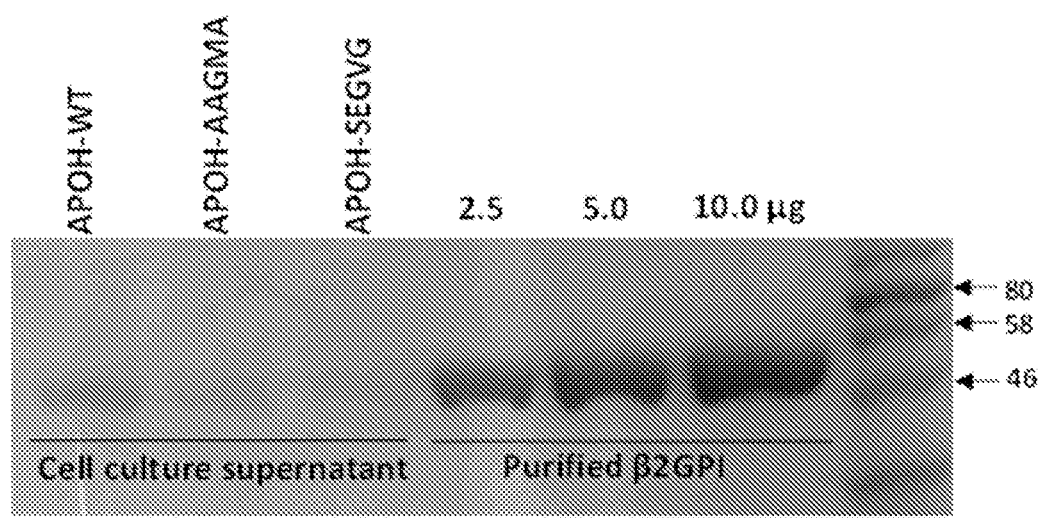
FIG. 12 shows Coomassie brilliant blue staining of 20 μl cell culture supernatants of spmAPOH-WT/AAGMA/SEGVG, as well as purified proteins isolated from these supernatants. This demonstrates efficient secretion of rAPOH when a modified signal peptide is employed.

Human Apolipoprotein H (APOH) ORF clone in a pCMV6-Entry vector with a Myc-DDK-tag was purchased from OriGene Technologies (Rockvile, Md.; Catalogue #RC205017). Full length cDNA was amplified using forward primer: 5'CACCATGGAGACA-GACACACTCCTGC-TATGGGTACTGCTGCTCTGGGTTCCAG GTTCCACTGGTCGGACCTGTCCCAAGCCAG3' (SEQ ID NO:15) and reverse primer: 5'TTAGCATGGCTTTA-CATCGGATGCATCAGTTTTC-CAAAAAGCCAGAGAACTGTG TTCCTTGAAGCAT-TTG3' (SEQ ID NO:16) with no tag and a native stop codon. The sequence of the forward primer includes the sequence encoding the mutant signal peptide (ATGGAGACA-GACACACTCCTGC-TATGGGTACTGCTGCTCTGGGTTCCAGGTTCC ACT;

SEQ ID NO:17) that replaced the native APOH signal peptide. In two constructs, we also performed site-directed mutagenesis to replace specific amino acids thought to be of importance in recognition of β2-glycoprotein I by pathogenic antiphospholipid antibodies (FIG. 10).

Amplified cDNA was sub-cloned into the pENTR™ Directional TOPO® cloning vector (Invitrogen, Catalogue #K2400-20, Carlsbad, Calif., USA). Upon confirmation of the correct DNA sequence, plasmid clone pENTR-spmAPOH-WT (FIG. 11) was used as template for subsequent APOH mutant generation by site directed mutagenesis. Evidence suggests that amino acids in the region 39-43 (RGGMR) of domain 1 of APOH comprise an important site for recognition by pathologic anti-β2GPI antibodies. We generated two mutants spanning the 39 to 43 amino acid region: SEGVG (R39S; G40E; M42V; R43G) and AAGMA (R39A; G40A; R43A). For spmAPOH-SEGVG mutant primer pairs, we used the forward primer: 5'AGCGAAGGGGTGGGAAAGTTTATCTGCCCTCTC3' (SEQ ID NO:18) and the reverse primer: 5'TTCCCACCCCTTCGCTGGACACATAGCCCGG3' (SEQ ID NO:19), and for spmAPOH-AAGMA we used the forward primer: 5' GCAGCAGGGATGGCAAAGTT-TATCTGCCCTCTC3' (SEQ ID NO:20) and reverse primer: 5'TTGCCATCCCTGCTGCGGACACATAGCCCGG3' (SEQ ID NO:21). The PCR reaction mix containing mutagenic primers was digested with DpnI (methylation-dependent endonuclease) to digest template plasmid DNA spmAPOH-WT. DH5α $E.$ $coli$ cells were transformed with digested PCR reaction mix and plasmids were sequenced. Upon sequence confirmation, pENTR-spmAPOH-WT; pENTR-spmAPOH-SEGVG and pENTR-spmAPOH-AAGMA clones were recombined with PLenti CMV Puro DEST vector (Addgene, Plasmid #17452, Cambridge, Mass., USA) using Gateway® LR Clonase® enzyme mix (Invitrogen, Catalogue #11791-019, Carlsbad, Calif., USA). The final recombined pDEST-spmAPOH clones were confirmed by sequencing and positive clones were used for lentivirus production.

D. Lentivirus Production

Lentivirus was produced using the Lentiviral Gateway Expression kit (Life Technologies, Carlsbad, Calif., USA). Twelve million GP2-293 (HEK) cells were seeded in 15 cm$^2$ plates with growth medium using 10% calf serum without antibiotics and grown overnight. Growth media was removed and replaced with Opti-MEM with reduced serum, and cells were cotransfected with 9 μg each of pLP1, pLP2, pVSVG, and pDEST-APOH-WT/SEGVG/AAGMA plasmid DNA using 150 μl of Lipofectamine™ 2000 (Thermo Fisher Scientific, Catalogue #11668019, Waltham, Mass., USA). Three days later, the supernatant was collected, centrifuged to remove cell debris and concentrated using a Lenti-X concentrator (Clontech Laboratories, Catalogue #631231, Mountain View, Calif., USA) according to the manufacturer's recommendations. The lentivirus pellet was resuspended in PBS and stored at −80° C. until further use.

E. Generation of Stable Cell Lines

HEK-293F cells were transduced with APOH lentiviral vectors in the presence of 5 μg/ml polybrene according to standard procedures. Briefly, 24 after treating cells with lentivirus, media was replaced with DMEM media containing 10% FBS and penicillin and streptomycin. After reaching confluence, cells were split 1:5 and grown in DMEM containing 10% FBS and selected against 2 μg/ml puromycin for 4 to 5 passages. Puromycin resistant cells expressing recombinant apoH were isolated as stable cell lines.

F. Recombinant Protein Expression and Purification

Stable cells lines were grown and expanded in DMEM containing 5% FBS and 2 μg/ml puromycin. Cells were transferred to EX-CELL 293 serum free media (Sigma, St. Louis, Mo.; catalogue #14571C) and grown as suspension culture in Optimum Growth™ 1.6 L Flasks (Fisher Scientific; Waltham, Mass.; Catalogue #NC0768461) at a density of 1.4×10$^6$ cells/ml on an orbital shaker rotating at 150 rpm, for 4 to 5 days. Cells were harvested by centrifugation at 5000 rpm for 10 min and secreted β2GPI present in cell culture supernatant was collected and filtered through a 0.2 μM filter. Filtered supernatant was concentrated using Centricon Plus-70 filter units and the medium was exchanged for buffer A (0.1 M Tris-HCl pH 7.8; 30 mM NaCl). Fifty milliliters of concentrated, buffer-exchanged cell culture supernatant was loaded onto a 5 ml heparin Hi-Trap column using a GE FPLC system, and protein eluted using a 10-50% NaCl gradient. Fractions within the peak containing β2GPI were run on 10% SDS-PAGE and stained using coomassie brilliant blue. Fractions containing pure β2GPI were pooled.

II. Isolation of Anti-β2GPI Antibodies

A. Affinity Purification of Patient-Derived Anti-β2GPI Antibodies

Serum from patients with antiphospholipid antibody syndrome (APS) was dialyzed overnight against 20 mM potassium phosphate buffer, pH 7.0, and incubated with Affigel-immobilized β2GPI in a 10 ml column with affinity column with end-over-end rotation overnight at 4° C. The column was washed with 100 ml 20 mM potassium phosphate buffer, pH 7.0. Bound anti-β2GPI antibodies were eluted in 1 ml fractions using 0.1 M citrate buffer pH 3.4 and collected in Eppendorf tubes containing neutralization buffer (1 M Tris-HCl, pH 9.0).

B. Fractionation of Anti-β2GPI-IgG from Total Anti-β2GPI Antibodies

Fractions containing anti-β2GPI antibodies (IgG, IgA, IgM) were pooled and diluted with 20 mM potassium phosphate buffer pH 7.0 and passed through a Protein-G column. The column was washed with 20 volumes of 20 mM potassium phosphate buffer pH 7.0 and eluted in 1 ml fractions with 0.1 M Glycine, pH 2.4, into eppendorf tubes containing neutralization buffer (1 M Tris-Cl, pH 9.0).

C. Anti-β2GPI-ELISA

Figure 13:
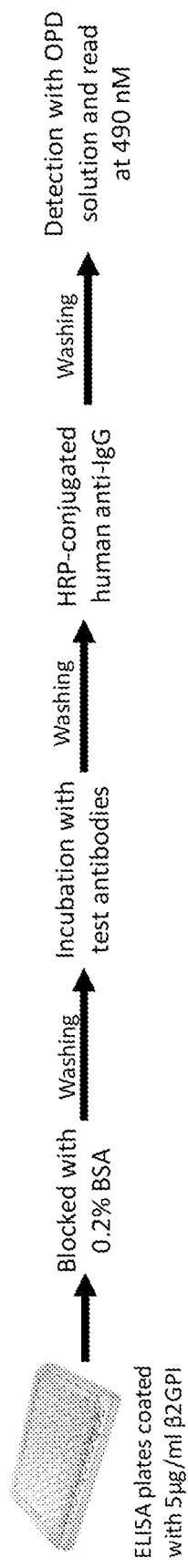
FIG. 13 provides a schematic of an exemplary anti-β2GPI-ELISA.

High binding ELISA plates were coated with 5 μg/ml β2GPI for 1 hour at 37° C. and non-specific binding blocked using 0.2% BSA for 1 hour at 37° C. β2GPI for these studies was either plasma-derived or recombinant (rβ2GPI); the recombinant β2GPI was from the spmAPOH-WT or spmAPOH-SEGVG vectors. After wells were coated with β2GPI, they were washed once with wash buffer (PBST, 0.05% tween-20). Anti-β2GPI antibodies (1 μg/ul) were diluted 1:50; 1:500; 1:1000; 1:5000 and 1:10,000 and 50 ul of diluted antibody was added to microplate wells and incubated at 37° C. for 30 minutes, followed by 3 washes with wash buffer. HRP-conjugated goat-anti-human/rabbit IgG was then added to wells and incubated at 37° C. for 30 minutes followed by 3 additional washes with wash buffer. Secondary antibody binding was detected by incubating wells with OPD solution (0.4 mg/ml in 50 mM phosphate citrate buffer) at room temperature for 10 mM, and the reaction stopped using 1N H2SO4 followed by detection at 490 nm. FIG. 13 provides a schematic of an exemplary anti-β2GPI-ELISA.

III. Binding of Anti-β2GPI Antibodies to Plasma and Recombinant WT β2GPI

A. Comparison of Binding to Plasma-Derived and Recombinant β2GPI

Figure 14:
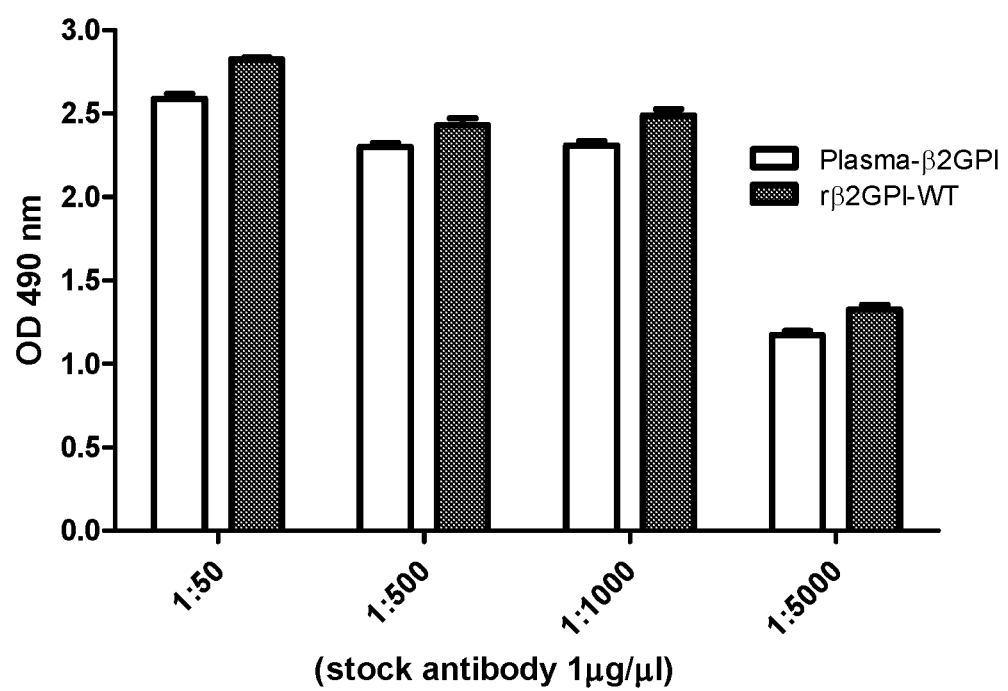
FIG. 14: Binding of affinity-purified anti-β2GPI antibodies from an APS patient, used at various dilutions, to plasma-derived and recombinant β2GPI.

The binding of patient derived anti-β2GPI antibodies to plasma derived β2GPI and recombinant WT β2GPI was initially characterized using the β2GPI-ELISA described above. Equivalent binding of antibodies to the recombinant and plasma-derived protein was observed (FIG. 14).

B. Recognition of rβ2GPI-WT by Plasma from Patients Undergoing Testing for Anti-β2GPI Antibodies To assess the interaction of anti-β2GPI antibodies in plasma with plasma-purified and recombinant β2GPI, we analyzed plasma from 32 patients referred to the Cleveland Clinic Special Coagulation Laboratory for anti-β2GPI testing using the Inova Quanta-Lite ELISA. Normal plasma samples (n=15) were also analyzed at 1:100 dilution to determine cutoffs for anti-β2GPI positivity. Briefly, 96-well plates were coated overnight at 4° C. with 2 ug/ml plasma-purified or recombinant β2GPI. After blocking β2GPI-coated plates with BSA, 50 ul of patient plasma at 1:10 and 1:100 dilutions were added to individual wells in quadruplicate. Results from different plates were standardized by extrapolating the amount of bound Ab from a standard curve prepared on each plate.

To compare performance of recombinant β2GPI versus plasma-purified β2GPI in the ELISA we first evaluated the correlation using Spearman's test. The results of the two ELISAs were also compared using the Wilcoxon matched pairs test. ELISA readings were considered positive if they were >$90^{th}$ percentile on a curve established using 15 normal plasma samples. Sensitivity and specificity of the assays was determined with respect to the results of the clinical assay.

The anti-β2GPI IgG ELISA using plasma purified and recombinant β2GPI demonstrated excellent correlation at both 1:10 (Spearman's rho 0.70, $P<0.001$) and 1:100 dilution (Spearman rho 0.727, $p<0.001$) (FIG. 3). Using the Wilcoxon test for paired samples, there was no significant difference between results of the ELISA using plasma-purified or recombinant β2GPI at 1:10 dilution (mean difference 4.26±22.25, $P<0.001$) and only a small difference at 1:100 dilution (mean difference 13.51±7.59, $P<0.001$). Of the 32 patient samples, 6 were known positive for anti-β2GPI IgG (titer≥20 GPL). Using a $90^{th}$ percentile cutoff established using healthy volunteer samples, the ELISA using recombinant β2GPI correctly identified 6/6 positive samples (sensitivity 100%). The ELISA using plasma-derived β2GPI correctly identified 5/6 positive samples (sensitivity 83.3%, specificity 84%).

C. Binding of Antibodies to Recombinant β2GPI-WT and rβ2GPI-SEGVG

Figure 15:
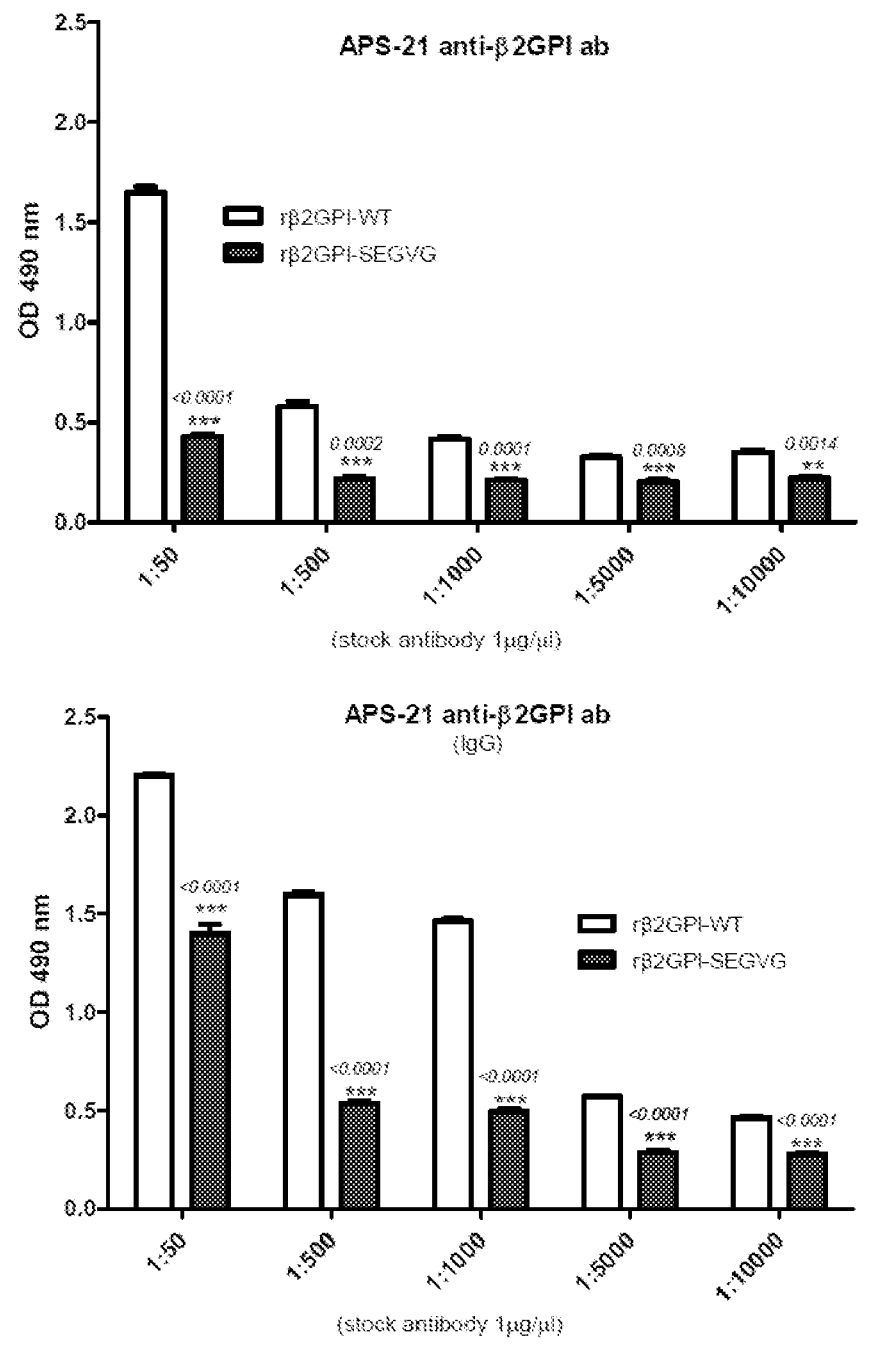

The binding of affinity-purified anti-β2GPI antibodies to recombinant β2GPI-WT and rβ2GPI-SEGVG was characterized using the β2GPI-ELISA described above. These studies demonstrated significantly greater binding of anti-β2GPI antibodies to rβ2GPI-WT protein compared to rβ2GPI-SEGVG (FIG. 15). Interestingly, anti-β2GPI IgG showed higher binding compared to total anti-β2GPI-antibodies, which included IgM anti-β2GPI. These results demonstrate that anti-β2GPI-antibodies from patients with APS depend on a native domain 1 β2GPI sequence for optimal binding.

Figure 16:
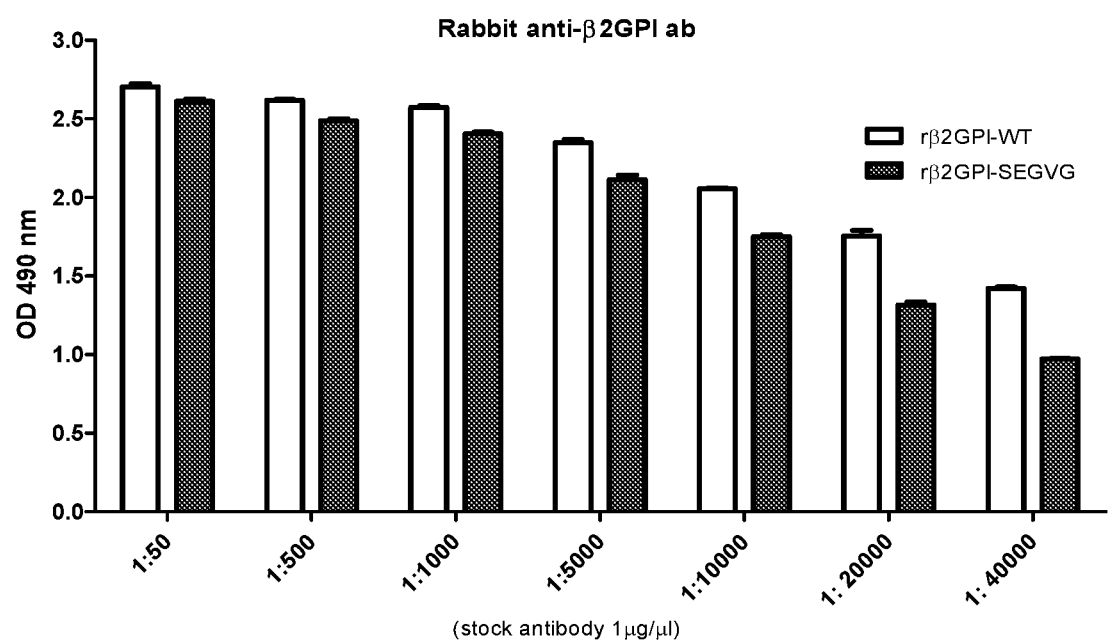
FIG. 16: Anti-β2GPI ELISA assessing reactivity of rabbit anti-β2GPI antibodies against rβ2GPI-WT and rβ2GPI-SEGVG (SEQ ID NO:37).

To exclude the possibility that these results might reflect major conformational changes in the mutant protein, we performed identical studies using polyclonal rabbit anti-β2GPI antibodies raised against human β2GPI that are not expected to be domain 1 specific. Though minor differences in binding of the rabbit antibody to rβ2GPI-WT and rβ2GPI-SEGVG were observed at very high antibody dilutions, we generally observed very little differences in binding of these antibodies to the two proteins (FIG. 16). These results suggest that differences in binding of patient-derived antibodies to the domain 1 mutant are specific for the human antibodies and potentially specific to pathologic human anti-β2GPI antibodies

D. Biosensor Analysis

Figure 17:
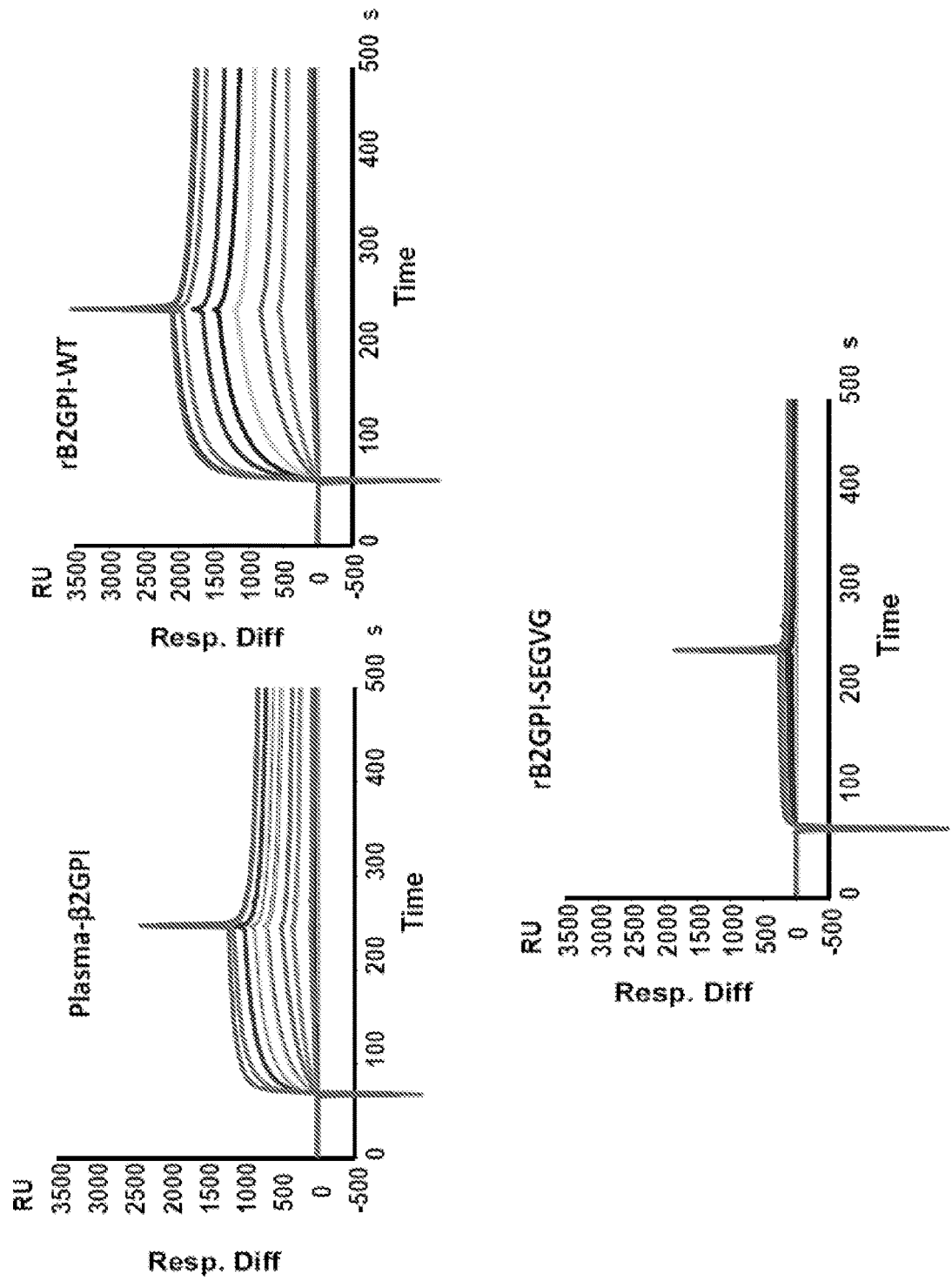
FIG. 17: Biosensor analysis of APS-21 patient-derived IgG anti-β2GPI antibody binding to plasma β2GPI, rβ2GPI-WT and rβ2GPI-SEGVG (SEQ ID NO:37).

To obtain a more detailed understanding of the interactions between patient-derived antibodies and recombinant β2GPI, we used biosensor analysis. Briefly, β2GPI was linked to carboxymethylated dextran coated CMS sensor chips using amine coupling in the presence of 1.0 M acetate buffer, pH 5.0. Four flow channels were coated with plasma derived-β2GPI, rβ2GPI-WT and rβ2GPI-SEGVG, respectively, with the additional channel used as control for comparison. β2GPI-coated channels were coupled to the chip in sufficient mass to cause a change of 1500 to 2000 Resonance Units (RU). Anti-β2GPI antibodies at concentrations ranging from 1-15,000 nM, were flowed through channels at the rate of 30 µl/minute for 3 min in the presence of running buffer (20 mmol/L HEPES, pH 7.4, supplemented with 300 mmol/L NaCl, 0.2% Tween-20 and 0.1% human serum albumin). After equilibrium binding was achieved, we assessed dissociation over a 10 minute interval. After dissociation, the sensor chip was regenerated using 10 ul of 50 mM Glycine-NaOH buffer containing 0.5% Triton X-100, pH 12.0, followed by 10 ul of 10 mM Glycine, pH 1.7. The BIAevaluation program (Biacore 3.0.1) was used to calculate association and dissociation rates to determine kinetic parameters of binding. FIG. 17 depicts the binding isotherms of antibodies from APS patient #21 to the different forms of recombinant β2GPI.

Figure 18:
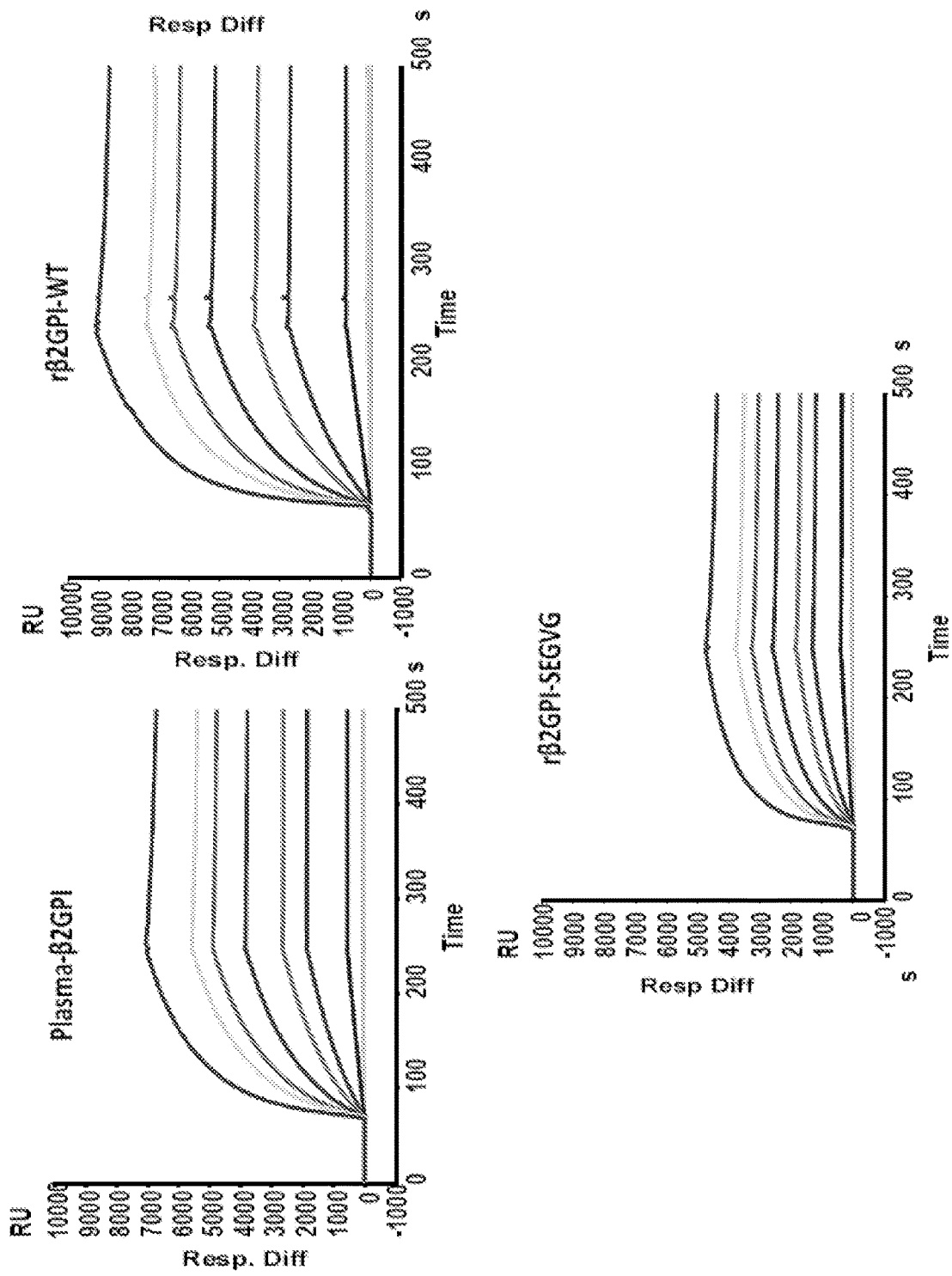
FIG. 18: Biosensor binding analysis of Rabbit anti-β2GPI antibodies using plasma derived-β2GPI, rβ2GPI-WT and rβ2GPI-SEGVG (SEQ ID NO:37).

As with ELISAs, to determine that the SEGVG mutation did not cause a global change in β2GP conformation, we measured the binding of a polyclonal rabbit-anti-β2GPI antibody to rβ2GPI-WT and rβ2GPI-SEGVG using this approach. Unlike patient derived anti-β2GPI antibodies, the polyclonal rabbit antibody recognized all forms of β2GPI with similar affinity although the Rmax was slightly decreased for the SEGVG mutant (FIG. 18). Analysis of the biosensor data revealed the kinetic parameters depicted in Table 2.

TABLE 2

Binding of anti-β2GPI antibodies to plasma, and recombinant wild-type and SEGVG mutant β2GPI

| Sample | Plasma β2GPI | | rβ2GPI-WT | | rβ2GPI-SEGVG | |
| --- | --- | --- | --- | --- | --- | --- |
| | KD (M) | Rmax | KD (M) | Rmax | KD (M) | Rmax |
| Rabbit-anti-β2GPI (IgG) | $7.03 \times 10^{-8}$ | 2970 | $7.8 \times 10^{-8}$ | 4360 | $5.06 \times 10^{-9}$ | 2120 |
| APS-21-anti-β2GPI (IgG) | $1.18 \times 10^{-8}$ | 509 | $2.08 \times 10^{-8}$ | 768 | $4.94 \times 10^{-6}$ | 56.3 |
| Human IgG isotype control | ND | No binding | ND | No binding | ND | No binding |

Taken together, this data demonstrates the following: 1) recombinant β2GPI is recognized as well as plasma β2GPI by affinity-purified human anti-β2GPI IgG, 2) the β2GPI mutant SEGVG is recognized with approximately 100-fold less affinity by human APS anti-β2GPI IgG, 3) plasma-derived and recombinant WT and mutant β2GPI are recognized equally well by a rabbit polyclonal anti-β2GPI antibody, suggesting that the conformation of the mutant is similar to that of the wild-type protein and that all domains are appropriately presented for binding. These conclusions demonstrate, for example, that the recombinant β2GPI provides a suitable substrate for diagnostic assays to distinguish domain 1-dependent vs non-domain 1-dependent binding of human APS IgG to β2GPI, and thus to identify the most pathogenic APS IgG antibodies. Moreover, this recombinant β2GPI can be expressed in high quantities, is easily purified, and provides a potentially-important tool for research studies focused on the role of anti-β2GPI antibodies in APS.

Figure 19:
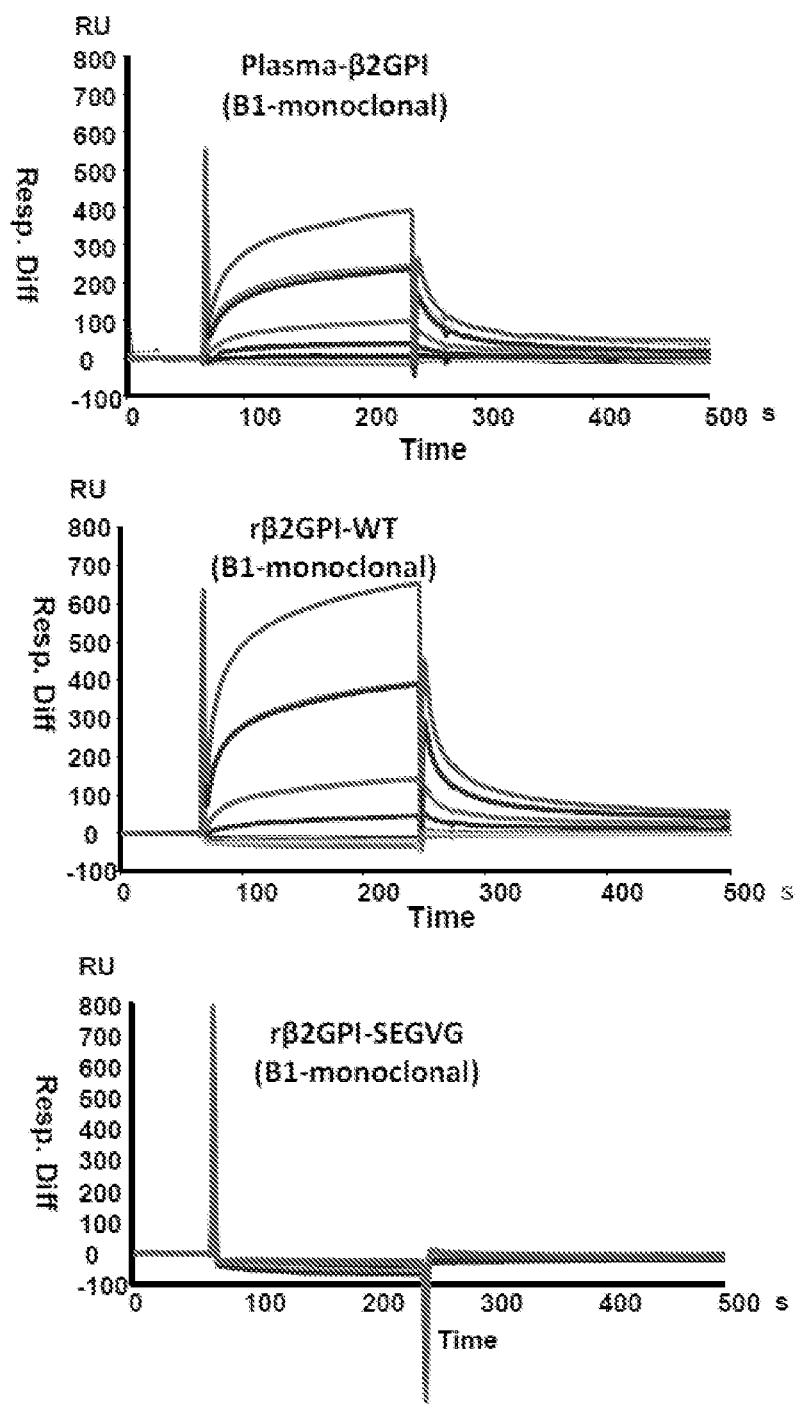
FIG. 19: Biosensor binding analysis of APS patient derived monoclonal antibodies B1 and IS6 using plasma derived-β2GPI, rβ2GPI-WT and rβ2GPI-SEGVG (SEQ ID NO:37).
Figure 19:
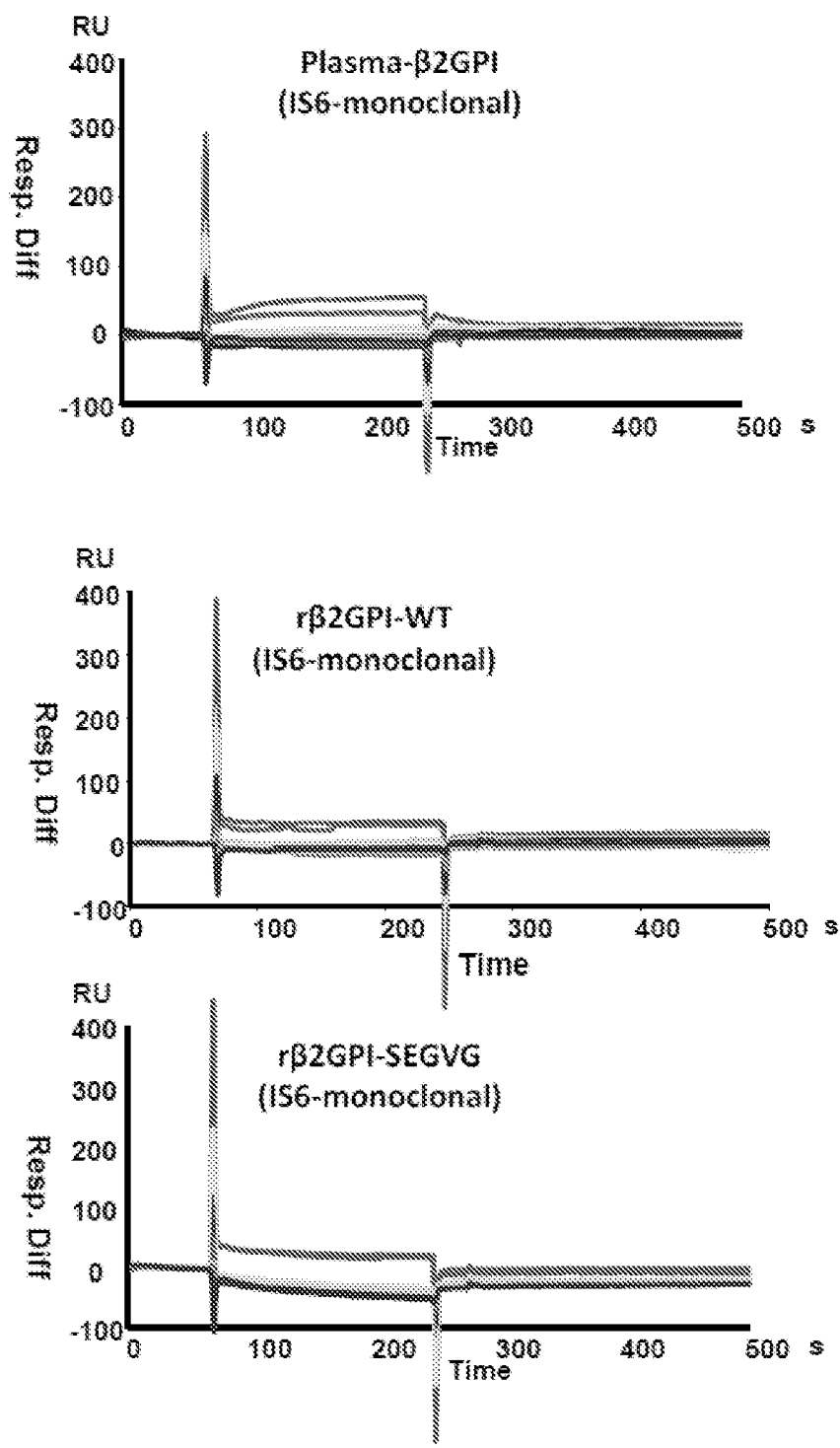
Figure 20:
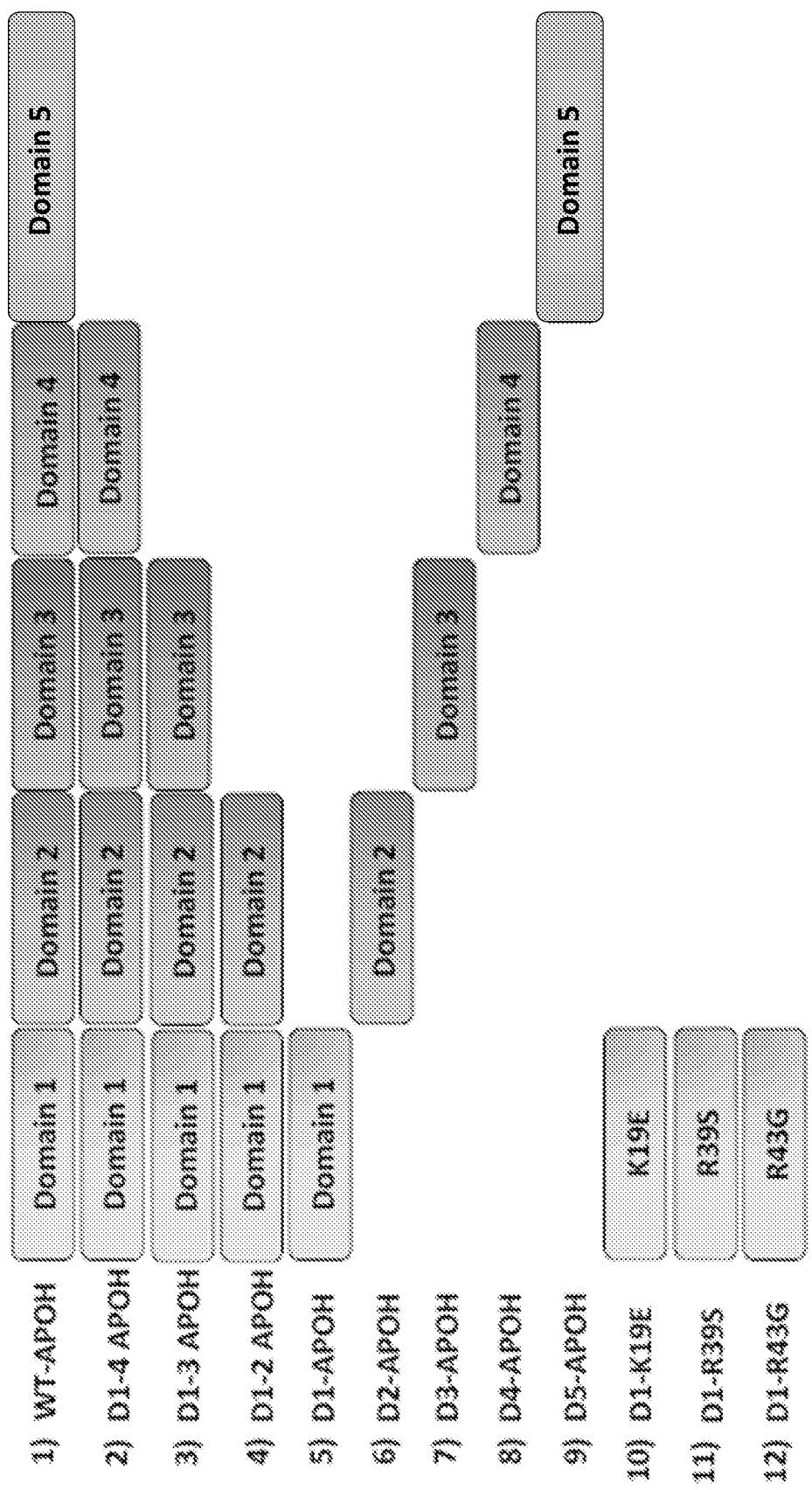
FIG. 20: Potential β2GPI mutants that can be prepared for example, as diagnostics, and/or as potential therapeutic inhibitors of anti-β2GPI antibody binding to β2GPI

E. Binding of Monoclonal Anti-β2GPI Antibodies to Plasma, rβ2GPI-WT and rβ2GPI-SEGVG Several human monoclonal antibodies to β2GPI have been developed. Whether these are representative of anti-β2GPI antibodies from APS patients is unknown. Nevertheless, they provide additional information concerning the utility of rβ2GPI. The specificity of these antibodies has not been thoroughly studied. Binding of two such antibodies, B-1 and IS-6, is depicted in FIG. 19.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A composition comprising: a nucleic acid sequence encoding a non-natural peptide, wherein said non-natural peptide comprises:
   a) a signal peptide portion comprising the amino acid sequence METDTLLLWVLLLW (SEQ ID NO:36), and
   b) a peptide of interest portion comprising at least a part of human β2-glycoprotein I (β2GPI) (SEQ ID NO:2), wherein said part of human β2GPI comprises domain I of human β2-glycoprotein I (SEQ ID NO:3) except comprising at least one of the following mutations numbered with reference to SEQ ID NO:2: R39S, R39A, G40E, G40A, M42V, R43G, and R43A.

2. The composition of claim 1, wherein said at least one of the following mutations comprises the following four mutations: R39S, G40E, M42V, and R43G mutations.

3. The composition of claim 1, wherein said at least one of the following mutations comprises the following three mutations: R39A, G40A, and R43A mutations.

4. The composition of claim 1, wherein said peptide of interest portion comprises human β2-glycoprotein I, except comprising at least one of the following mutations: R39S, R39A, G40E, G40A, M42V, R43G, and R43A.

5. The composition of claim 1, wherein said signal peptide portion comprises one of the following amino acid sequences:

```
a)      METDTLLLWVLLLWVPGS;      (SEQ ID NO: 33)

b)      METDTLLLWVLLLWVPG;       (SEQ ID NO: 34)
        and d)      METDTLLLWVLLLWVP.        (SEQ ID NO: 35)
```

6. The composition of claim 1, wherein said signal peptide portion comprises METDTLLLWVLLLWVPGST (SEQ ID NO:32).

7. A method of expressing human β2-glycoprotein I (β2GPI) comprising:

culturing a cell containing an expression vector encoding β2GPI linked to a signal peptide comprising METDTLLLWVLLLWVPGST (SEQ ID NO: 32) such that said β2GPI is expressed in, and exported from, said cell, and purifying said exported β2GPI such that at least 20 mg/L of said β2GPI is recovered.

8. The method of claim 7, wherein said β2GPI is able to specifically bind to anti-Apolipoprotein H antibodies from a patient with antiphospholipid syndrome.

* * * * *

UNITED STATES PATENT AND TRADEMARK OFFICE
CERTIFICATE OF CORRECTION

| | | |
|---|---|---|
| PATENT NO. | : 11,661,447 B2 | Page 1 of 1 |
| APPLICATION NO. | : 16/635796 | |
| DATED | : May 30, 2023 | |
| INVENTOR(S) | : McCrae et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 499 days.

Signed and Sealed this
Twelfth Day of November, 2024

Katherine Kelly Vidal
*Director of the United States Patent and Trademark Office*

SEQUENCE LISTING

<160> NUMBER OF SEQ ID NOS: 38

<210> SEQ ID NO 1
<211> LENGTH: 345
<212> TYPE: PRT
<213> ORGANISM: Homo sapiens

<400> SEQUENCE: 1

```
Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30

Thr Val Val Pro Leu Lys Thr Phe Tyr Glu Pro Gly Glu Glu Ile Thr
        35                  40                  45

Tyr Ser Cys Lys Pro Gly Tyr Val Ser Arg Gly Gly Met Arg Lys Phe
    50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
    130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220
```

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
    290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
                340                 345

<210> SEQ ID NO 2
<211> LENGTH: 326
<212> TYPE: PRT
<213> ORGANISM: Homo sapiens

<400> SEQUENCE: 2

Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110

Pro Glu Leu Pro Val Cys Ala Pro Ile Ile Cys Pro Pro Pro Ser Ile
        115                 120                 125

Pro Thr Phe Ala Thr Leu Arg Val Tyr Lys Pro Ser Ala Gly Asn Asn
    130                 135                 140

Ser Leu Tyr Arg Asp Thr Ala Val Phe Glu Cys Leu Pro Gln His Ala
145                 150                 155                 160

Met Phe Gly Asn Asp Thr Ile Thr Cys Thr Thr His Gly Asn Trp Thr
                165                 170                 175

Lys Leu Pro Glu Cys Arg Glu Val Lys Cys Pro Phe Pro Ser Arg Pro
            180                 185                 190

Asp Asn Gly Phe Val Asn Tyr Pro Ala Lys Pro Thr Leu Tyr Tyr Lys
        195                 200                 205

Asp Lys Ala Thr Phe Gly Cys His Asp Gly Tyr Ser Leu Asp Gly Pro
    210                 215                 220

Glu Glu Ile Glu Cys Thr Lys Leu Gly Asn Trp Ser Ala Met Pro Ser
225                 230                 235                 240

```
Cys Lys Ala Ser Cys Lys Leu Pro Val Lys Ala Thr Val Val Tyr
            245                 250                 255

Gln Gly Glu Arg Val Lys Ile Gln Glu Lys Phe Lys Asn Gly Met Leu
        260                 265                 270

His Gly Asp Lys Val Ser Phe Phe Cys Lys Asn Lys Glu Lys Lys Cys
        275                 280                 285

Ser Tyr Thr Glu Asp Ala Gln Cys Ile Asp Gly Thr Ile Glu Val Pro
        290                 295                 300

Lys Cys Phe Lys Glu His Ser Ser Leu Ala Phe Trp Lys Thr Asp Ala
305                 310                 315                 320

Ser Asp Val Lys Pro Cys
                325

<210> SEQ ID NO 3
<211> LENGTH: 61
<212> TYPE: PRT
<213> ORGANISM: Artificial sequence
<220> FEATURE:
<223> OTHER INFORMATION: Synthetic

<400> SEQUENCE: 3

Arg Thr Cys Pro Lys Pro Asp Asp Leu Pro Phe Ser Thr Val Val Pro
1               5                   10                  15

Leu Lys Thr Phe Tyr Glu Pro Gly Glu Glu Ile Thr Tyr Ser Cys Lys
            20                  25                  30

Pro Gly Tyr Val Ser Arg Gly Gly Met Arg Lys Phe Ile Cys Pro Leu
        35                  40                  45

Thr Gly Leu Trp Pro Ile Asn Thr Leu Lys Cys Thr Pro
    50                  55                  60

<210> SEQ ID NO 4
<211> LENGTH: 13
<212> TYPE: PRT
<213> ORGANISM: Artificial sequence
<220> FEATURE:
<223> OTHER INFORMATION: Synthetic

<400> SEQUENCE: 4

Gly Tyr Val Ser Arg Gly Gly Met Arg Lys Phe Ile Cys
1               5                   10

<210> SEQ ID NO 5
<211> LENGTH: 15
<212> TYPE: PRT
<213> ORGANISM: Artificial sequence
<220> FEATURE:
<223> OTHER INFORMATION: Synthetic

<400> SEQUENCE: 5

Pro Gly Tyr Val Ser Arg Gly Gly Met Arg Lys Phe Ile Cys Pro
1               5                   10                  15

<210> SEQ ID NO 6
<211> LENGTH: 19
<212> TYPE: PRT
<213> ORGANISM: Homo sapiens

<400> SEQUENCE: 6

Met Ile Ser Pro Val Leu Ile Leu Phe Ser Ser Phe Leu Cys His Val
1               5                   10                  15

Ala Ile Ala
```

<210> SEQ ID NO 7
<211> LENGTH: 19
<212> TYPE: PRT
<213> ORGANISM: Homo sapiens

<400> SEQUENCE: 7

Met Glu Thr Asp Thr Leu Leu Leu Trp Val Leu Leu Trp Val Pro
1               5                   10                  15

Gly Ser Thr

<210> SEQ ID NO 8
<211> LENGTH: 19
<212> TYPE: PRT
<213> ORGANISM: Pan troglodytes

<400> SEQUENCE: 8

Met Ile Ser Pro Val Leu Ile Leu Phe Ser Ser Phe Leu Cys His Val
1               5                   10                  15

Ala Ile Ala

<210> SEQ ID NO 9
<211> LENGTH: 19
<212> TYPE: PRT
<213> ORGANISM: Macaca mulatta

<400> SEQUENCE: 9

Met Ile Ser Pro Val Leu Ile Leu Phe Ser Ser Phe Leu Cys His Val
1               5                   10                  15

Ala Ile Ala

<210> SEQ ID NO 10
<211> LENGTH: 19
<212> TYPE: PRT
<213> ORGANISM: Gorilla gorilla

<400> SEQUENCE: 10

Met Ile Ser Pro Val Leu Ile Leu Phe Ser Ser Phe Leu Cys His Val
1               5                   10                  15

Ala Ile Ala

<210> SEQ ID NO 11
<211> LENGTH: 19
<212> TYPE: PRT
<213> ORGANISM: Equus ferus caballus

<400> SEQUENCE: 11

Met Ile Ser Pro Val Leu Ile Leu Phe Ser Ser Phe Leu Cys His Val
1               5                   10                  15

Ala Ile Ala

<210> SEQ ID NO 12
<211> LENGTH: 19
<212> TYPE: PRT
<213> ORGANISM: Mus musculus

<400> SEQUENCE: 12

Met Val Ser Pro Val Leu Ala Leu Phe Ser Ala Phe Leu Cys His Val
1               5                   10                  15

Ala Ile Ala

```
<210> SEQ ID NO 13
<211> LENGTH: 19
<212> TYPE: PRT
<213> ORGANISM: Rattus norvegicus

<400> SEQUENCE: 13

Met Ile Ser Pro Ala Leu Ile Phe Phe Ser Ala Phe Leu Cys His Val
1               5                   10                  15

Ala Ile Ala

<210> SEQ ID NO 14
<211> LENGTH: 19
<212> TYPE: PRT
<213> ORGANISM: Bos Taurus

<400> SEQUENCE: 14

Met Leu Pro Pro Ala Leu Val Leu Leu Leu Gly Phe Leu Cys His Val
1               5                   10                  15

Ala Ile Ala

<210> SEQ ID NO 15
<211> LENGTH: 83
<212> TYPE: DNA
<213> ORGANISM: Artificial sequence
<220> FEATURE:
<223> OTHER INFORMATION: Synthetic

<400> SEQUENCE: 15
caccatggag acagacacac tcctgctatg ggtactgctg ctctgggttc caggttccac      60
tggtcggacc tgtcccaagc cag                                             83

<210> SEQ ID NO 16
<211> LENGTH: 70
<212> TYPE: DNA
<213> ORGANISM: Artificial sequence
<220> FEATURE:
<223> OTHER INFORMATION: Synthetic

<400> SEQUENCE: 16
ttagcatggc tttacatcgg atgcatcagt tttccaaaaa gccagagaac tgtgttcctt      60
gaagcatttg                                                            70

<210> SEQ ID NO 17
<211> LENGTH: 57
<212> TYPE: DNA
<213> ORGANISM: Artificial sequence
<220> FEATURE:
<223> OTHER INFORMATION: Synthetic

<400> SEQUENCE: 17
atggagacag acacactcct gctatgggta ctgctgctct gggttccagg ttccact         57

<210> SEQ ID NO 18
<211> LENGTH: 33
<212> TYPE: DNA
<213> ORGANISM: Artificial sequence
<220> FEATURE:
<223> OTHER INFORMATION: Synthetic

<400> SEQUENCE: 18
agcgaagggg tgggaaagtt tatctgccct ctc                                  33
```

```
<210> SEQ ID NO 19
<211> LENGTH: 31
<212> TYPE: DNA
<213> ORGANISM: Artificial sequence
<220> FEATURE:
<223> OTHER INFORMATION: Synthetic

<400> SEQUENCE: 19
ttcccacccc ttcgctggac acatagcccg g                              31

<210> SEQ ID NO 20
<211> LENGTH: 33
<212> TYPE: DNA
<213> ORGANISM: Artificial sequence
<220> FEATURE:
<223> OTHER INFORMATION: Synthetic

<400> SEQUENCE: 20
gcagcaggga tggcaaagtt tatctgccct ctc                            33

<210> SEQ ID NO 21
<211> LENGTH: 31
<212> TYPE: DNA
<213> ORGANISM: Artificial sequence
<220> FEATURE:
<223> OTHER INFORMATION: Synthetic

<400> SEQUENCE: 21
ttgccatccc tgctgcggac acatagcccg g                              31

<210> SEQ ID NO 22
<211> LENGTH: 25
<212> TYPE: PRT
<213> ORGANISM: Artificial sequence
<220> FEATURE:
<223> OTHER INFORMATION: Synthetic

<400> SEQUENCE: 22

Thr Tyr Ser Cys Lys Pro Gly Tyr Val Ser Arg Gly Gly Met Arg Lys
 1               5                  10                  15

Phe Ile Cys Pro Leu Thr Gly Leu Trp
            20                  25

<210> SEQ ID NO 23
<211> LENGTH: 20
<212> TYPE: PRT
<213> ORGANISM: Artificial sequence
<220> FEATURE:
<223> OTHER INFORMATION: Synthetic

<400> SEQUENCE: 23

Val Ser Phe Phe Cys Lys Asn Lys Glu Lys Lys Cys Ser Tyr Thr Glu
 1               5                  10                  15

Asp Ala Gln Cys
            20

<210> SEQ ID NO 24
<211> LENGTH: 30
<212> TYPE: PRT
<213> ORGANISM: Artificial sequence
<220> FEATURE:
<223> OTHER INFORMATION: Synthetic

<400> SEQUENCE: 24

Leu His Gly Asp Lys Val Ser Phe Phe Cys Lys Asn Lys Glu Lys Lys
 1               5                  10                  15
```

```
Cys Ser Tyr Thr Glu Asp Ala Gln Cys Ile Asp Gly Thr Ile
            20                  25                  30

<210> SEQ ID NO 25
<211> LENGTH: 40
<212> TYPE: PRT
<213> ORGANISM: Artificial sequence
<220> FEATURE:
<223> OTHER INFORMATION: Synthetic

<400> SEQUENCE: 25

Phe Lys Asn Gly Met Leu His Gly Asp Lys Val Ser Phe Cys Lys
1               5                   10                  15

Asn Lys Glu Lys Lys Cys Ser Tyr Thr Glu Asp Ala Gln Cys Ile Asp
            20                  25                  30

Gly Thr Ile Glu Val Pro Lys Cys
            35                  40

<210> SEQ ID NO 26
<211> LENGTH: 58
<212> TYPE: PRT
<213> ORGANISM: Artificial sequence
<220> FEATURE:
<223> OTHER INFORMATION: Synthetic

<400> SEQUENCE: 26

Arg Val Cys Pro Phe Ala Gly Ile Leu Glu Asn Gly Ala Val Arg Tyr
1               5                   10                  15

Thr Thr Phe Glu Tyr Pro Asn Thr Ile Ser Phe Ser Cys Asn Thr Gly
            20                  25                  30

Phe Tyr Leu Asn Gly Ala Asp Ser Ala Lys Cys Thr Glu Glu Gly Lys
        35                  40                  45

Trp Ser Pro Glu Leu Pro Val Cys Ala Pro
    50                  55

<210> SEQ ID NO 27
<211> LENGTH: 63
<212> TYPE: PRT
<213> ORGANISM: Artificial sequence
<220> FEATURE:
<223> OTHER INFORMATION: Synthetic

<400> SEQUENCE: 27

Ile Ile Cys Pro Pro Pro Ser Ile Pro Thr Phe Ala Thr Leu Arg Val
1               5                   10                  15

Tyr Lys Pro Ser Ala Gly Asn Asn Ser Leu Tyr Arg Asp Thr Ala Val
            20                  25                  30

Phe Glu Cys Leu Pro Gln His Ala Met Phe Gly Asn Asp Thr Ile Thr
        35                  40                  45

Cys Thr Thr His Gly Asn Trp Thr Lys Leu Pro Glu Cys Arg Glu
    50                  55                  60

<210> SEQ ID NO 28
<211> LENGTH: 60
<212> TYPE: PRT
<213> ORGANISM: Artificial sequence
<220> FEATURE:
<223> OTHER INFORMATION: Synthetic

<400> SEQUENCE: 28

Val Lys Cys Pro Phe Pro Ser Arg Pro Asp Asn Gly Phe Val Asn Tyr
1               5                   10                  15
```

```
Pro Ala Lys Pro Thr Leu Tyr Tyr Lys Asp Lys Ala Thr Phe Gly Cys
            20                  25                  30

His Asp Gly Tyr Ser Leu Asp Gly Pro Glu Glu Ile Glu Cys Thr Lys
        35                  40                  45

Leu Gly Asn Trp Ser Ala Met Pro Ser Cys Lys Ala
    50                  55                  60
```

<210> SEQ ID NO 29
<211> LENGTH: 83
<212> TYPE: PRT
<213> ORGANISM: Artificial sequence
<220> FEATURE:
<223> OTHER INFORMATION: Synthetic

<400> SEQUENCE: 29

```
Ser Cys Lys Val Pro Val Lys Lys Ala Thr Val Val Tyr Gln Gly Glu
1               5                   10                  15

Arg Val Lys Ile Gln Glu Lys Phe Lys Asn Gly Met Leu His Gly Asp
            20                  25                  30

Lys Val Ser Phe Phe Cys Lys Asn Lys Glu Lys Lys Cys Ser Tyr Thr
        35                  40                  45

Glu Asp Ala Gln Cys Ile Asp Gly Thr Ile Glu Val Pro Lys Cys Phe
    50                  55                  60

Lys Glu His Ser Ser Leu Ala Phe Trp Lys Thr Asp Ala Ser Asp Val
65                  70                  75                  80

Lys Pro Cys
```

<210> SEQ ID NO 30
<211> LENGTH: 5
<212> TYPE: PRT
<213> ORGANISM: Artificial sequence
<220> FEATURE:
<223> OTHER INFORMATION: Synthetic

<400> SEQUENCE: 30

```
Arg Gly Gly Met Arg
1               5
```

<210> SEQ ID NO 31
<211> LENGTH: 11
<212> TYPE: PRT
<213> ORGANISM: Artificial sequence
<220> FEATURE:
<223> OTHER INFORMATION: Synthetic

<400> SEQUENCE: 31

```
Leu Leu Leu Trp Val Leu Leu Leu Val Trp Pro
1               5                   10
```

<210> SEQ ID NO 32
<211> LENGTH: 19
<212> TYPE: PRT
<213> ORGANISM: Artificial sequence
<220> FEATURE:
<223> OTHER INFORMATION: Synthetic

<400> SEQUENCE: 32

```
Met Glu Thr Asp Thr Leu Leu Leu Trp Val Leu Leu Leu Trp Val Pro
1               5                   10                  15

Gly Ser Thr
```

```
<210> SEQ ID NO 33
<211> LENGTH: 18
<212> TYPE: PRT
<213> ORGANISM: Artificial sequence
<220> FEATURE:
<223> OTHER INFORMATION: Synthetic

<400> SEQUENCE: 33

Met Glu Thr Asp Thr Leu Leu Leu Trp Val Leu Leu Leu Trp Val Pro
1               5                   10                  15

Gly Ser

<210> SEQ ID NO 34
<211> LENGTH: 17
<212> TYPE: PRT
<213> ORGANISM: Artificial sequence
<220> FEATURE:
<223> OTHER INFORMATION: Synthetic

<400> SEQUENCE: 34

Met Glu Thr Asp Thr Leu Leu Leu Trp Val Leu Leu Leu Trp Val Pro
1               5                   10                  15

Gly

<210> SEQ ID NO 35
<211> LENGTH: 16
<212> TYPE: PRT
<213> ORGANISM: Artificial sequence
<220> FEATURE:
<223> OTHER INFORMATION: Synthetic

<400> SEQUENCE: 35

Met Glu Thr Asp Thr Leu Leu Leu Trp Val Leu Leu Leu Trp Val Pro
1               5                   10                  15

<210> SEQ ID NO 36
<211> LENGTH: 14
<212> TYPE: PRT
<213> ORGANISM: Artificial sequence
<220> FEATURE:
<223> OTHER INFORMATION: Synthetic

<400> SEQUENCE: 36

Met Glu Thr Asp Thr Leu Leu Leu Trp Val Leu Leu Leu Trp
1               5                   10

<210> SEQ ID NO 37
<211> LENGTH: 5
<212> TYPE: PRT
<213> ORGANISM: Artificial sequence
<220> FEATURE:
<223> OTHER INFORMATION: Synthetic

<400> SEQUENCE: 37

Ser Glu Gly Val Gly
1               5

<210> SEQ ID NO 38
<211> LENGTH: 5
<212> TYPE: PRT
<213> ORGANISM: Artificial sequence
<220> FEATURE:
<223> OTHER INFORMATION: Synthetic
```

```
<400> SEQUENCE: 38

Ala Ala Gly Met Ala
1               5
```